US008906384B2

(12) United States Patent
De Los Santos et al.

(10) Patent No.: US 8,906,384 B2
(45) Date of Patent: Dec. 9, 2014

(54) ANTIVIRAL ACTIVITY OF BOVINE TYPE III INTERFERON AGAINST FOOT-AND-MOUTH DISEASE VIRUS

(75) Inventors: Teresa B. De Los Santos, Miller Place, NY (US); James J. Zhu, Niantic, CT (US); Fayna Diaz-San Segundo, Ronkonkoma, NY (US); Marvin J. Grubman, Southold, NY (US); Marla J. Koster, Cutchogue, NY (US)

(73) Assignee: The United States of America as represented by The Secretary of Agriculture, Washington, CO (US)

( * ) Notice: Subject to any disclaimer, the term of this patent is extended or adjusted under 35 U.S.C. 154(b) by 845 days.

(21) Appl. No.: 12/976,129

(22) Filed: Dec. 22, 2010

(65) Prior Publication Data

US 2012/0164171 A1    Jun. 28, 2012

(51) Int. Cl.

| | |
|---|---|
| A61K 39/12 | (2006.01) |
| C12N 15/63 | (2006.01) |
| A61P 31/12 | (2006.01) |
| C07H 21/04 | (2006.01) |
| A61K 31/7088 | (2006.01) |
| C07K 14/555 | (2006.01) |
| A61K 38/00 | (2006.01) |

(52) U.S. Cl.
CPC ............ *C07K 14/555* (2013.01); *A61K 38/00* (2013.01)
USPC .................. 424/204.1; 435/320.1; 536/23.52

(58) Field of Classification Search
None
See application file for complete search history.

(56) References Cited

U.S. PATENT DOCUMENTS

| 7,833,533 B2 * | 11/2010 | Grubman et al. ........... 424/216.1 |
| 2004/0001864 A1 * | 1/2004 | King et al. ................. 424/204.1 |
| 2012/0164171 A1 * | 6/2012 | De Los Santos et al. .. 424/204.1 |

FOREIGN PATENT DOCUMENTS

WO    WO 2009/0124309    * 10/2009

OTHER PUBLICATIONS

Zhu et al. (Virology. May 2010; 404: 32-40).*
Segundo et al. (Journal of Virology. Feb. 2010; 84 (4): 2063-2077).*

* cited by examiner

*Primary Examiner* — Shanon A Foley
(74) *Attorney, Agent, or Firm* — John D. Fado; Evelyn M. Rabin

(57) ABSTRACT

A member of the bovine type III IFN family, boIFN-$\lambda$3, was identified and characterized. We expressed boIFN-$\lambda$3 using a recombinant replication defective human adenovirus type 5 (Ad5) and demonstrated antiviral activity against foot-and-mouth disease virus (FMDV) and vesicular stomatitis virus (VSV) in bovine cells in vitro. Cattle were inoculated with Ad5-boIFN-$\lambda$3 followed by intradermolingual or aerosol FMDV challenge. Results demonstrated that the type III IFN family is conserved in bovines and that treatment of cattle with boIFN-$\lambda$3 alone or in combination with IFN-$\alpha$ is able to confer delayed and reduced severity of FMD. Furthermore inoculation with Ad5-boIFN-$\lambda$3 alone conferred full protection against aerosol challenge for at least 7 days after administration suggesting that type III IFN used in combination with FMD vaccines could fill one of the current gaps in emergency vaccination against FMDV.

13 Claims, 12 Drawing Sheets
(10 of 12 Drawing Sheet(s) Filed in Color)

Fig. 1A

Global Protein alignment.  Reference molecule: boIL28B aa, Region 1 to 195
Sequences: 5.  Scoring matrix: BLOSUM 62

Sequence View: Similarity Format, Color areas of high matches at same base position

```
boIL28B aa        1  ------------------------------------------------------mapgctlvlvlmttvalsrtga
pred.boIL28B      1  mppplrldperserraagaallrgltepgglsaatrmrwclrrsflkdqeespgtsdmapgrtlvlvlmttvalsrtga
muIL28B aa        1  ---------------------------------------------------------mlllllplllaavltrtqa
poIL28B aa        1  -------------------------------------------------------malggslvlvlmtvapprtga
huIL28B aa        1  mkld---------------------------------------------------mtgdcmpvlvlm--aavltvtga boIL28B aa       24  vpvpsapralppargchvaqfkslspqelqafktardafedsflpkdwdosthlfprtrdlkhlqvwerpvaleaelalt
pred.boIL28B     81  vpvpsapralppargchmaqfkslspqelqafktardafedsflpkdwdosthlfprtrdlkhlqvwerpvaleaelalt
muIL28B aa       20  dpvgratrlpveakdchiaqfkslspkelqafkkakgaiekrllekdmrceshlisrawdlkqlqvqerpkalgasvalt
poIL28B aa       24  vpvpealralpgargchlaqfkslspqalqafkrakdafeesll-edwncssrifpltrdlkqlqvwerpvaleaevalt
huIL28B aa       26  vpvarlrgalpdargchiaqfkslspqelqafkrakdaleesllkdckcrsrlfpstwdlrqlqvrerpvaleaelalt boIL28B aa      104  itvleamans--sighsleqplltlqnlheklqacvpaqptassrprgr-lhhwlhrlqea-r-kesgdcleasvmfnll
pred.boIL28B    161  itvleamans--sighsleqplltlqnlheklqacvpaqptassrprgr-lhhwlhrlqea-r-kesgdcleasvmfnll
muIL28B aa      100  lkyweninds--alttilgqplhtlshlnsqlqtctqlgataepkpsrrlsrwlhrlgea-qsketpgcledevtanlf
poIL28B aa      103  lavlgslans--slheeldqplhtlrblhaqlqacvpaqpmagpkpprgr-lhhwlhrlgeaqk-kepgscleasvmfnlf
huIL28B aa      106  lkvlestadtdpalgdvldqplhtlhhalsqlradiqpgrtagpptrgr-lhhwlhrlqeapk-kespgcleasvtfnlf boIL28B aa      179  rlltrdlkcvasgdqcv         SEQ ID NO: 2 (195aa)
pred.boIL28B    236  rlltrdlkcvasgdqcv         SEQ ID NO: 4
muIL28B aa      177  qlltrdlkcvasgdqcv         SEQ ID NO: 6
poIL28B aa      179  rlltrdlkcvasgdlcv         SEQ ID NO: 8
huIL28B aa      184  rlltrdlncvasgdlcv         SEQ ID NO: 10
```

Fig. 1B

Global DNA alignment. Reference molecule: boIL28B cds, Region 1 to 588
Sequences: 5. Scoring matrix: Linear (Mismatch 2, OpenGap 4, ExtGap 1)

| Sequence | Start | End | #Match | NonMatch | %Match |
|---|---|---|---|---|---|
| boIL28B cds | 1 | 588 | | | |
| pred. boIL28B | 1 | 759 | 586 | 173 | 77 |
| huIL28B | 1 | 591 | 473 | 124 | 79 |
| muIL28B | 1 | 582 | 422 | 176 | 70 |
| poIL28B | 1 | 588 | 503 | 88 | 85 |

Assembled DNA alignment. Reference molecule: boIL28B cds, Region 1 to 588
Sequences: 5. Method: FastScan - Max Qual

| Sequence | Start | End | #Match | NonMatch | %Match |
|---|---|---|---|---|---|
| boIL28B cds | 1 | 588 | | | |
| pred. boIL28B | 1 | 759 | 586 | 173 | 77 |
| huIL28B | 1 | 591 | 476 | 125 | 79 |
| poIL28B | 1 | 588 | 503 | 88 | 85 |
| muIL28B | 1 | 582 | 427 | 162 | 72 |

Global DNA alignment. Reference molecule: boIL28B cds, Region 1 to 588
Sequences: 5. Scoring matrix: Linear (Mismatch 2, OpenGap 4, ExtGap 1)

| Sequence | Start | End | #Match | NonMatch | %Match |
|---|---|---|---|---|---|
| boIL28B cds | 1 | 588 | | | |
| pred. boIL28B | 1 | 759 | 586 | 173 | 77 |
| huIL28B | 1 | 591 | 473 | 124 | 79 |
| muIL28B | 1 | 582 | 422 | 176 | 70 |
| poIL28B | 1 | 588 | 503 | 88 | 85 |

Fig. 1C

Global Protein alignment. Reference molecule: boIL28B aa, Region 1 to 195
Sequences: 5. Scoring matrix: BLOSUM 62

| Sequence | Start | End | #Match | NonMatch | %Match |
| --- | --- | --- | --- | --- | --- |
| boIL28B aa | 1 | 195 | | | |
| muIL28B aa | 1 | 193 | 111 | 86 | 56 |
| poIL28B aa | 1 | 195 | 150 | 46 | 76 |
| huIL28B aa | 1 | 200 | 134 | 68 | 66 |
| pred.boIL28B aa | 1 | 252 | 193 | 59 | 76 |

Global Protein alignment. Reference molecule: boIL28B aa, Region 1 to 195
Sequences: 5. Scoring matrix: BLOSUM 62

| Sequence | Start | End | #Match | NonMatch | %Match |
| --- | --- | --- | --- | --- | --- |
| boIL28B aa | 1 | 195 | | | |
| muIL28B aa | 1 | 193 | 111 | 86 | 56 |
| poIL28B aa | 1 | 195 | 150 | 46 | 76 |
| huIL28B aa | 1 | 200 | 134 | 68 | 66 |
| pred.boIL28B aa | 1 | 252 | 193 | 59 | 76 |

Assembled Protein alignment. Reference molecule: pred.boIL28B aa, Region 1 to 252
Sequences: 5. Method: FastScan - Max Qual (Cons N)

| Sequence | Start | End | #Match | NonMatch | %Match |
| --- | --- | --- | --- | --- | --- |
| pred.boIL28B aa | 1 | 252 | | | |
| huIL28B aa | 1 | 200 | 136 | 115 | 54 |
| poIL28B aa | 1 | 195 | 150 | 89 | 62 |
| boIL28B aa | 1 | 195 | 193 | 2 | 98 |
| muIL28B aa | 1 | 193 | 110 | 83 | 56 |

Fig. 1D

Fig. 4

| Treatment | CCL2 | CCL3 | CCL20 | CxCL10 | IL28B | IL28Rα | IFNβ | IL10Rα | IRF7 | ISG15 | MDA 5 | MX 1 | OAS 1 | PKR |
|---|---|---|---|---|---|---|---|---|---|---|---|---|---|---|
| 5u boIFN-A3 | 1.1 | 1.0 | 0.8 | 4.7 | 1.0 | 1.1 | 0.5 | 1.0 | 4.6 | 735.1 | 18.2 | 53.6 | 334.3 | 8.4 |
| 10u boIFN-A3 | 1.3 | 0.9 | 1.1 | 6.6 | 0.1 | 0.8 | 0.6 | 0.9 | 5.8 | 1114.0 | 26.2 | 67.4 | 394.8 | 10.4 |
| 50u boIFN-A3 | 1.7 | 0.8 | 1.5 | 8.5 | 1.7 | 0.9 | 2.5 | 1.2 | 8.5 | 2073.5 | 61.2 | 103.1 | 758.6 | 16.1 |
| 100u boIFN-A3 | 1.9 | 1.0 | 2.6 | 8.6 | 1.5 | 1.2 | 0.4 | 1.2 | 9.8 | 2513.7 | 68.6 | 111.6 | 761.4 | 16.9 |
| 5u poIFN-α | 2.0 | 1.1 | 1.7 | 5.8 | 1.6 | 0.9 | 1.0 | 1.2 | 8.4 | 2189.6 | 53.2 | 111.4 | 735.0 | 16.2 |
| 10u poIFN-α | 2.0 | 1.1 | 1.2 | 8.1 | 0.4 | 1.0 | 0.7 | 1.2 | 9.7 | 3114.6 | 79.3 | 126.0 | 860.9 | 18.8 |
| 50u poIFN-α | 4.4 | 1.2 | 2.8 | 121.5 | 1.6 | 1.2 | 0.8 | 1.2 | 14.7 | 4469.5 | 132.7 | 145.2 | 1090.4 | 23.0 |
| 100u poIFN-α | 4.6 | 1.2 | 5.2 | 178.7 | 0.8 | 1.1 | 1.1 | 1.4 | 15.1 | 5081.6 | 127.9 | 137.9 | 1022.8 | 23.1 |
| 5u boIFN-α | 0.9 | 0.8 | 0.8 | 4.9 | 0.8 | 0.8 | 0.7 | 0.7 | 3.6 | 516.2 | 13.3 | 43.2 | 308.8 | 6.7 |
| 10u boIFN-α | 1.1 | 0.8 | 1.9 | 10.0 | 0.8 | 0.9 | 0.7 | 0.7 | 4.8 | 881.1 | 24.1 | 56.6 | 430.4 | 9.5 |
| 50u boIFN-α | 1.9 | 0.8 | 2.0 | 9.3 | 1.1 | 0.9 | 1.7 | 0.9 | 7.2 | 1721.1 | 48.8 | 80.2 | 638.4 | 12.3 |
| 100u boIFN-α | 1.7 | 0.8 | 2.3 | 27.8 | 0.8 | 0.9 | 1.7 | 0.9 | 7.2 | 1740.1 | 53.6 | 69.6 | 675.7 | 13.6 |
| 5u boIFN-A3 + 5u poIFN-α | 1.4 | 0.8 | 1.5 | 2.8 | 0.9 | 0.9 | 0.5 | 0.8 | 5.9 | 1237.3 | 33.4 | 73.0 | 519.2 | 9.7 |
| 5u boIFN-A3 + 5u boIFN-α | 1.1 | 0.8 | 1.8 | 2.9 | 0.5 | 0.7 | 0.9 | 0.8 | 3.9 | 656.6 | 16.0 | 39.9 | 328.4 | 7.5 |
| 50u boIFN-A3 + 50u poIFN-α | 3.0 | 0.8 | 4.0 | 53.8 | 0.6 | 0.9 | 0.8 | 1.0 | 11.0 | 3031.4 | 94.0 | 99.1 | 905.1 | 18.3 |
| 50u boIFN-A3 + 50u boIFN-α | 1.4 | 0.6 | 0.8 | 8.3 | 0.7 | 0.6 | 0.2 | 0.7 | 8.4 | 1906.5 | 44.6 | 64.7 | 532.0 | 11.4 |

Fold induction ≥ 2 with boIFN-A3 treatment
Fold induction ≥ 2 with poIFN-α treatment
Fold induction ≥ 2 with boIFN-α treatment
Fold induction ≥ 2 with boIFN-A3 and boIFN-α treatment

| TISSUES | CCL 2[a] | | | CCL 3 | | | CCL 20 | | | CXCL 10 | | | IL 28 B | | |
|---|---|---|---|---|---|---|---|---|---|---|---|---|---|---|---|
| | α[b] | λ[c] | α+λ | α | λ | α+λ | α | λ | α+λ | α | λ | α+λ | α | λ | α+λ |
| Dorsal Soft Palate | 1.1 | 2.5 | 1.9 | 1.2 | 2.6 | 0.4 | 1.0 | 0.6 | 0.6 | 0.8 | 12.0 | 2.1 | 0.1 | 0.9 | 18.3 |
| Nasopharynx | 8.1 | 24.9 | 8.5 | 24.9 | 114.0 | 2.9 | 170.8 | 736.2 | 35.8 | 36.8 | 82.8 | 4.4 | 29.3 | 499.0 | 51.3 |
| Oropharynx | 0.6 | 0.6 | 1.2 | 3.7 | 4.6 | 3.1 | 57.5 | 130.4 | 66.2 | 1.3 | 2.9 | 3.3 | 1117.2 | 17.6 | 509.1 |
| Larynx | 1.2 | 7.6 | 2.7 | 10.0 | 10.9 | 8.9 | 3.4 | 3.7 | 4.9 | 10.2 | 8.0 | 16.0 | 58.4 | 3.4 | 7.0 |
| Trachea | 0.6 | 2.8 | 1.6 | 2.8 | 3.2 | 2.8 | 35.7 | 319.9 | 137.1 | 3.7 | 5.3 | 12.1 | 0.0 | 0.1 | 0.0 |
| Proximal Lung | 0.5 | 0.6 | 0.8 | 0.2 | 0.3 | 0.4 | 2.8 | 1.3 | 3.3 | 0.3 | 0.3 | 1.1 | 0.1 | 0.2 | 2.2 |
| Tongue | 0.6 | 0.8 | 1.0 | 0.7 | 0.6 | 1.3 | 1.1 | 1.8 | 1.2 | 0.6 | 0.8 | 1.1 | 12.7 | 3.7 | 6.5 |
| Retro Lymph Node | 0.9 | 0.8 | 0.8 | 0.6 | 0.7 | 0.3 | 1.2 | 0.2 | 0.2 | 0.4 | 0.9 | 0.3 | 0.0 | 0.2 | 3.9 |
| Palatine Tonsil | 5.6 | 9.8 | 21.7 | 109.7 | 60.6 | 75.6 | 7266.9 | 22520.9 | 20859.6 | 28.3 | 15.9 | 49.5 | 28.7 | 362.8 | 2760.0 |
| Spleen | 1.2 | 0.6 | 3.6 | 1.1 | 0.9 | 1.0 | 8.1 | 2.9 | 41.6 | 1.4 | 0.7 | 3.1 | 26.3 | 5.6 | 2119.8 |
| Skin Interdigital | 6.1 | 2.2 | 9.8 | 2.3 | 1.0 | 0.6 | 2.3 | 1.3 | 6.3 | 5.4 | 0.9 | 4.8 | 0.4 | 0.2 | 1.6 |
| Skin Coronary Band | 0.7 | 9.3 | 7.4 | 1.9 | 7.6 | 1.2 | 0.7 | 13.9 | 11.0 | 1.0 | 3.2 | 1.4 | 1.9 | 4.7 | 5.7 |

| TISSUES | IL 28 r Alpha | | | IFN Beta | | | IL 10 r Beta | | | IRF 7 | | | ISG 15 | | |
|---|---|---|---|---|---|---|---|---|---|---|---|---|---|---|---|
| | α | λ | α+λ | α | λ | α+λ | α | λ | α+λ | α | λ | α+λ | α | λ | α+λ |
| Dorsal Soft Palate | 0.2 | 0.2 | 2.2 | 2.1 | 2.3 | 174.2 | 6.6 | 7.7 | 3.8 | 0.3 | 0.0 | 226.7 | 0.8 | 1.0 | 6.0 |
| Nasopharynx | 52.7 | 49.9 | 22.0 | 17.6 | 180.5 | 15.2 | 28.1 | 25.8 | 13.9 | 0.7 | 0.5 | 3464.7 | 9.0 | 8.5 | 30.8 |
| Oropharynx | 11.8 | 6.9 | 10.0 | 25.7 | 6.4 | 17.1 | 5.3 | 6.2 | 11.6 | 3.2 | 0.7 | 5147.1 | 7.9 | 17.6 | 23.6 |
| Larynx | 0.7 | 0.6 | 1.4 | 6.3 | 2.6 | 3.8 | 1.3 | 2.7 | 2.3 | 0.5 | 0.0 | 326.5 | 1.1 | 1.1 | 4.1 |
| Trachea | 0.2 | 0.2 | 0.5 | 0.1 | 0.4 | 0.4 | 0.7 | 1.6 | 1.6 | 0.1 | 0.3 | 370.0 | 0.4 | 2.1 | 5.0 |
| Proximal Lung | 0.3 | 0.2 | 1.2 | 1.5 | 1.4 | 2.2 | 4.6 | 4.9 | 2.1 | 1.8 | 0.1 | 374.6 | 2.8 | 0.6 | 4.5 |
| Tongue | 1.6 | 2.2 | 1.3 | 1.9 | 4.0 | 2.3 | 3.0 | 3.6 | 1.7 | 2.1 | 0.6 | 903.4 | 1.8 | 9.8 | 6.9 |
| Retro Lymph Node | 0.3 | 0.3 | 2.2 | 0.3 | 0.2 | 2.3 | 0.7 | 0.6 | 0.7 | 0.2 | 0.2 | 58.3 | 0.4 | 0.5 | 0.4 |
| Palatine Tonsil | 2.2 | 8.5 | 21.9 | 66.5 | 169.0 | 669.8 | 6.5 | 10.7 | 9.7 | 2.0 | 14.2 | 1100.0 | 1.9 | 4.1 | 10.3 |
| Spleen | 1.2 | 0.9 | 47.3 | 3.2 | 1.2 | 93.7 | 1.0 | 1.0 | 2.4 | 4.9 | 0.1 | 815.1 | 6.2 | 0.9 | 12.6 |
| Skin Interdigital | 2.1 | 1.5 | 1.0 | 1.1 | 0.2 | 0.4 | 1.6 | 1.0 | 0.9 | 1.0 | 0.0 | 282.6 | 11.4 | 5.3 | 7.9 |
| Skin Coronary Band | 0.4 | 0.7 | 0.8 | 1.7 | 3.2 | 4.9 | 1.0 | 2.1 | 1.4 | 0.2 | 0.1 | 311.6 | 1.5 | 3.3 | 15.6 |

Fig. 5

| TISSUES | MDA 5 | | | MX 1 | | | OAS 1 | | | PKR | | | RIG 1 | | |
|---|---|---|---|---|---|---|---|---|---|---|---|---|---|---|---|
| | α | λ | α+λ | α | λ | α+λ | α | λ | α+λ | α | λ | α+λ | α | λ | α+λ |
| Dorsal Soft Palate | 1.3 | 1.8 | 3.6 | 2.9 | 2.1 | 6.9 | 1.9 | 1.0 | 2.9 | 1.3 | 0.8 | 2.8 | 0.6 | 1.1 | 1.5 |
| Nasopharynx | 17.1 | 12.9 | 24.3 | 20.5 | 15.0 | 28.6 | 18.4 | 7.6 | 19.8 | 12.1 | 10.2 | 26.8 | 5.7 | 7.7 | 9.1 |
| Oropharynx | 4.8 | 19.4 | 19.0 | 5.7 | 9.7 | 12.4 | 4.4 | 5.7 | 9.0 | 3.6 | 8.7 | 4.7 | 5.8 | 4.4 | 66.2 |
| Larynx | 1.0 | 2.2 | 4.0 | 2.2 | 4.2 | 7.0 | 1.3 | 1.5 | 3.0 | 0.8 | 1.4 | 2.0 | 0.6 | 1.2 | 1.0 |
| Trachea | 1.1 | 3.4 | 4.8 | 1.1 | 1.3 | 3.6 | 1.0 | 1.0 | 2.5 | 0.6 | 1.2 | 1.8 | 0.1 | 0.5 | 0.2 |
| Proximal Lung | 1.5 | 0.6 | 3.7 | 2.3 | 1.0 | 4.2 | 1.5 | 0.5 | 2.0 | 1.5 | 0.8 | 2.1 | 1.0 | 1.5 | 1.6 |
| Tongue | 1.3 | 18.6 | 8.5 | 3.1 | 13.4 | 11.2 | 1.5 | 9.4 | 6.0 | 2.0 | 8.6 | 6.2 | 2.2 | 3.7 | 1.7 |
| Retro Lymph Node | 0.8 | 1.1 | 0.7 | 2.3 | 1.1 | 1.7 | 0.7 | 0.4 | 0.5 | 0.8 | 0.7 | 0.7 | 0.1 | 0.2 | 0.1 |
| Palatine Tonsil | 2.8 | 4.5 | 6.2 | 2.4 | 1.7 | 4.9 | 1.0 | 1.0 | 2.6 | 1.4 | 1.9 | 3.0 | 3.5 | 19.0 | 4.4 |
| Spleen | 3.6 | 0.9 | 6.4 | 3.9 | 0.7 | 5.9 | 2.6 | 0.5 | 3.2 | 1.6 | 0.6 | 2.6 | 3.5 | 1.8 | 8.5 |
| Skin Interdigital | 14.2 | 8.7 | 9.5 | 15.9 | 7.2 | 11.9 | 6.6 | 2.2 | 3.4 | 3.8 | 3.3 | 3.8 | 6.5 | 0.7 | 0.9 |
| Skin Coronary Band | 1.6 | 7.9 | 22.0 | 2.4 | 4.7 | 9.6 | 1.5 | 2.0 | 3.4 | 1.4 | 3.9 | 7.2 | 0.8 | 1.9 | 1.3 |

☐ Fold induction ≥ 2 with Ad5-polFNα treatment
▨ Fold induction ≥ 2 with Ad5-bolFNλ3 treatment
▨ Fold induction ≥ 2 with combination treatment
▨ Fold induction ≥ 2 and enhanced with combination treatment

[a] Gene abbreviation.
[b] Ad5-polFN-α.
[c] Ad5-bolFN-λ3 (IL28B)
[d] Combination.

ANTIVIRAL ACTIVITY OF BOVINE TYPE III INTERFERON AGAINST FOOT-AND-MOUTH DISEASE VIRUS

BACKGROUND OF THE INVENTION

1. Field of the Invention

This invention relates to an isolated, recombinant nucleic acid comprising a sequence that encodes bovine interferon-λ3 (boIFN-λ3), an antiviral pharmaceutical composition comprising a vector containing the isolated, recombinant nucleic acid encoding bovine interferon-λ3 (boIFN-λ3) and additional antiviral pharmaceutical compositions comprising a combination of a vector containing the isolated, recombinant nucleic acid encoding bovine interferon-λ3 (boIFN-λ3) and a vector containing other biotherapeutics such as the isolated, recombinant nucleic acid encoding porcine Type I interferons (poIFN-α/β), or the isolated, recombinant nucleic acid encoding bovine Type I interferons (boIFN-α/β), or the isolated, recombinant nucleic acid encoding foot and mouth disease virus (FMDV) antigen, wherein the compositions are capable of inducing systemic antiviral activity, specifically anti-foot and mouth disease virus (anti-FMDV) activity and of inducing up-regulation of specific gene expression in vivo, and thereby acting to delay and reduce severity of foot and mouth disease (FMD) and to the method of treating bovines, swine, goats, and sheep with the antiviral compositions of the invention in order to reduce or prevent the degree or rate of infection by FMDV and to reduce the severity of FMD or any symptom or condition resulting from infection by the FMDV in the treated animal as compared to an untreated infected animal.

2. Description of the Relevant Art

Foot-and-mouth disease virus (FMDV) is the etiologic agent of one of the most devastating diseases that affects cloven-hoofed livestock. Infection with FMDV causes an acute disease that spreads very rapidly and is characterized by fever, lameness and vesicular lesions on the feet, tongue, snout and teats, with high morbidity but low mortality (Grubman and Baxt. 2004. _Clinical Micro. Rev._ 17:465-493). With the exception of North America, Western Europe and Australia, FMD is enzootic in the rest of the world where disease control is achieved by inhibition of animal movement, slaughter of infected and in contact animals, disinfection of contaminated premises and vaccination with an inactivated whole virus antigen. However, use of this vaccine is not recommended in FMD free-countries due to technical limitations in differentiating vaccinated from infected animals and to the more severe trade restrictions for animals or animal products from areas where the vaccine is used, as established by the International Organization of Animal Health programs (World Organization for Animal Health (OIE). Foot and Mouth Disease. OIE Terrestrial Animal Health Code. Chapter 8.5 (2010). In recent years the OIE has recognized that, to be successful, FMD control programs should include the use of antivirals and/or immunomodulatory molecules in addition to newly developed marker vaccines (Scudamore and Harris. 2002. _Rev. Sci. Tech. Off. Int. Epiz._ 21: 699-710).

In all vertebrates, expression of interferons (IFNs) constitute the first line of defense against viral infection and, indeed, administration of IFNs as biotherapeutics has been effective in controlling several viral infections (Basler and Garcia-Sastre. 2002. _Int. Rev. Immunol._ 21: 305-337; Fensterl and Sen. 2009. _Biofactors_ 35:14-20). In the case of FMDV, we have previously demonstrated that treatment of bovine, porcine and ovine cells with type I or type II IFN dramatically inhibits viral replication (Chinsangaram et al. 1999. _J. Virol._ 73: 9891-9898; Chinsangaram et al. 2001. _J. Virol._ 75: 5498-5503; Moraes et al., 2007. _J. Virol._ 81: 7124-7135). Furthermore, swine inoculated with a replication defective human adenovirus 5 vector (Ad5) that delivers porcine IFN-α were sterilely protected when challenged with several FMDV serotypes 24 h post inoculation (Chinsangaram et al. 2001, supra; Moraes et al. 2003. _Vaccine_ 22:268-279; Dias et al. 2010. _J. Interferon Cytokine Res._ September 28. [Epub ahead of print]). Studies to understand the mechanism by which type I IFN protects swine against FMD have shown that at least some IFN-stimulated genes (ISGs) and migration of immune cells to the sites of infection play a significant role in controlling viral replication in swine (Chinsangaram et al. 1999, supra; de los Santos et al. 2006. _J. Virol._ 80: 1906-1914; Moraes et al. 2007, supra; Diaz-San Segundo et al. 2010. _J. Virol._ 84: 2063-2077). However, a similar approach has shown limitations in cattle where only delayed disease and reduced clinical signs have been observed (Wu et al. 2003. _J. Interferon Cytokine Res._ 7: 359-368).

Recently, a new family of IFNs has been described, type III IFN or IFN-λ (Kotenko et al. 2003. _Nat. Immunol._ 4:69-77; Sheppard et al. 2003. _Nat. Immunol._ 4:63-68). These IFNs are related to the type I/II IFN gene families and also to the interleukin 10 (IL10) family of ligands. Within the type III IFN family three structurally related members have been identified in humans, mice and chickens: IFN-λ1 (IL29), IFN-λ2 (IL28A) and IFN-λ3 (IL28B) (Kotenko et al., supra; Sheppard et al., supra; Sommereyns et al. 2008. PLoS Pathog. 4:e1000017; Karpala et al. 2008. _J. Interferon & Cytokine Res._ 28:341-350). Similar to type I IFN expression, the expression of type III IFN is induced in response to recognition of pathogen-associated molecular patterns and activation of transcription factors, such as nuclear factor κB (NF-κB), IFN regulatory factor-3 (IRF-3) and IFN regulatory factor-7 (IRF-7) (Iversen et al. 2010. J. Virology [Epub ahead of print]). Type III IFN signals through a heterodimeric cellular receptor that is composed of IL28-Rα, a type III IFN-specific subunit and IL10-Rβ, a subunit shared by other IL10 related cytokines. Despite the fact that type I and type III IFNs act on different receptors, they trigger strikingly similar responses through the activation of multiple members of the signal transducer and activator of transcription (STAT) family (Zhou et al. 2007. _J. Virology_ 81:7749-7758). However, expression of the type III IFN receptor in a tissue specific manner, mainly in epithelia, has been proposed as one of the mechanisms evolved by different organisms to possibly prevent and protect themselves from viral invasion through the skin and mucosal surfaces (Sommereyns et al., supra). Although not strictly robust, IFN-λ has been shown to induce protection against several viruses in cell culture, as well as in animal models, including herpes simplex virus type 2 (HSV-2), hepatitis B and hepatitis C (Ank et al. 2006. _J. Virol._ 80:4501-4509; Robeck et al. 2005. _J. Virol._ 79:3851-3854; Marcello et al. 2006. _Gastroenterology_ 131:1887-98). Furthermore, a role in modulating the balance of Th1/Th2 immune response has been recently proposed for IFN-λ1 biasing towards a stronger block on Th2 responses (Jordan et al. 2008. Genes and Immunity 8:254-261). No member of the type III IFN family has been described in bovines, and bovine genome sequencing has not provided evidence of predictive sequences for this type of IFN (The Bovine Genome Sequencing and Analysis Consortium et al. 2009. Science 324:522-526). However, very recently a predictive sequence of an IL28B-like mRNA has been deposited in GenBank, but no related literature is available (Accession#XM_002695050).

As discussed, FMDV is highly sensitive to the actions of type I and type II IFNs in vitro and in vivo; however, treatment with these IFNs only conferred partial protection in cattle. Thus, there is an active interest in developing and testing new antivirals with proven efficacy in this species. Here, we report the identification and cloning of a member of the bovine (bo) type III IFN family, boIFN-λ3, and the characterization of its anti-FMDV properties.

Adjuvant activity of IFNs has been shown against various viral infections including FMD (Toporovski et al. 2010. *Expert. Opin. Biol. Ther* 10:1489-1500; Cheng et al. 2007. Vaccine 25: 5199-5208; de Avila Boton et al. 2006. *Vaccine* 24: 3446-3456). Most of these studies included type I and type II IFNs. A satisfactory response against FMD was obtained in swine; therefore, similar results are expected in cattle (de Avila Boton et al, supra). Recent studies have shown that type III IFN displays adjuvant activity in humans (Morrow et al. 2009. *Blood* 113:5868-5877).

SUMMARY OF THE INVENTION

We have isolated and expressed a nucleic acid molecule which encodes bovine interferon-λ3 (boIFN-λ3) and displays antiviral activity in vitro and in vivo against FMDV when delivered by an Adenovirus (Ad)5 vector.

In accordance with this discovery, it is an object of the invention to provide an isolated, recombinant nucleic acid molecule encoding bovine interferon-λ3 (boIFN-λ3) and antiviral pharmaceutical compositions comprising the isolated, recombinant nucleic acid molecule encoding bovine interferon-λ3 (boIFN-λ3) wherein the compositions are capable of inducing systemic antiviral activity, specifically anti-foot and mouth disease virus (FMDV) activity, induction of adjuvanted adaptive immune responses against FMDV and up-regulation of specific gene expression in vivo, and thereby acting to delay, reduce severity and/or prevent foot and mouth disease.

An added object of the invention is to provide antiviral pharmaceutical compositions comprising a combination of a vector containing the isolated, recombinant nucleic acid molecule encoding bovine interferon-λ3 (boIFN-λ3) and a vector containing the isolated, recombinant nucleic acid molecule encoding porcine type I IFNs (α/β) or the isolated, recombinant nucleic acid molecule encoding bovine type I IFNs (α/β), or the isolated, recombinant nucleic acid molecule encoding FMDV antigen.

An additional object of the invention is to provide antiviral pharmaceutical compositions comprising constructs and vectors comprising the isolated, recombinant nucleic acid molecule encoding bovine interferon-λ3 (boIFN-λ3) and also the isolated, recombinant nucleic acid molecule encoding bovine interferon-λ3 (boIFN-λ3) and the isolated, recombinant nucleic acid molecule encoding porcine type I IFNs (α/β) and/or the isolated, recombinant nucleic acid molecule encoding bovine type I IFNs (α/β) and/or the isolated, recombinant nucleic acid molecule encoding FMDV antigen in combination.

A further object of the invention is to provide a rationally designed live FMDV vaccine comprising Ad5-boIFN-λ3 or Ad5-boIFN-λ3 and Ad5-porcine type I IFNs(α/β), or Ad5 bovine type I IFN(α/β), or Ad5-boIFN-λ3 in combination with Ad5-FMD vaccine or inactivated whole antigen FMDV vaccine.

Another object of the invention is to provide a method for treating an animal with the antiviral compositions of the invention in order to reduce the degree or rate of infection by FMDV and to reduce the severity of FMD or any symptom or condition resulting from infection by the FMDV in the treated animal as compared to an untreated infected animal.

It is a further object of the invention to reduce the degree or rate of infection by FMDV in cows and swine.

It is another object of the invention to decrease the severity of FMD in cows and swine.

It is an additional object of the invention to prevent FMD in cows and swine.

It is a yet another object of the invention to induce expression of IFN-stimulated genes correlated with systemic control of viral replication.

It is another object of the invention to induce expression of IFN-stimulated genes in skin and tissues of the upper airways of cows and swine.

Other objects and advantages of this invention will become readily apparent from the ensuing description.

BRIEF DESCRIPTION OF THE DRAWINGS

The patent or application file contains at least one drawing executed in color. Copies of this patent or patent application publication with color drawing(s) will be provided by the U.S. Patent and Trademark Office upon request and payment of the necessary fee.

FIGS. 1A-1D depict the DNA and amino acid sequence analysis of boIFN-λ3 (boIL28B). FIG. 1A depicts the nucleotide sequences aligned to known homologous sequences; FIG. 1B shows the deduced amino acid sequences aligned to known homologous sequences. The coding sequence of boIFN-λ3 comprising 585 nucleotides (SEQ ID NO:1 minus the stop codon tga) is translated into a 195 amino acid protein (SEQ ID NO: 2). A predicted signal peptide for secretion is contained between amino acids 1 and 24 of the boIFN-λ3 protein; the putative N-glycosylation site comprises amino acids 112-115 of the 195 amino acid boIFN-λ3 protein. Percent homologies in nucleotide (FIG. 1C) or amino acid (FIG. 1D) sequences were calculated using different algorithms in Clone Manager Suite 8®. Abbreviations: Pred.: predicted; hu: human; mu: murine; po: porcine; aa: amino acid; cds: coding sequence.

FIG. 2A shows the result of western blot analysis (using a polyclonal rabbit antibody) of cell lysates and supernatants evaluated for the presence of recombinant boIFN-λ3 protein. Antiviral activity of recombinant boIFN-λ3 protein (expressed in IBRS2 cells) was evaluated in primary EBK cells challenged with FMDV (FIG. 2B) and in MDBK cells challenged with VSV (FIG. 2C). FIG. 2D depicts the neutralization of antiviral activity with a specific anti-boIFN-λ3 polyclonal antibody in MDBK cells challenged with VSV. Asterisk (*) denotes neutralized antiviral activity.

FIG. 4 depicts the analysis of gene expression in bovine cells treated in vitro with IFNs. EBK cells were treated for 24 h with varying concentrations of boIFN-λ3, poIFN-α or boIFN-α alone or in combination. RNA was isolated and gene expression was analyzed by qRT-PCR. Primers and probes are described in Table 1. Results are expressed as relative fold induction of cells treated with IFN with respect to cells treated with medium (mock). Shaded colored areas represent induction relative to mock treated cells. Color coding indicates gene induction according to each treatment.

FIG. 5 depicts the analysis of gene expression in tissues isolated from bovines treated with Ad5-boIFN-λ3, Ad5-poIFN-α, or a combination of both IFNs. Gene expression was measured by qRT-PCR in RNA samples extracted from the listed bovine tissues. Results are expressed as relative fold induction values of Ad5 IFN treated with respect to Ad5-Blue-control treated animals. Color coding indicates levels of gene induction.

DETAILED DESCRIPTION OF THE INVENTION

Figure 2:
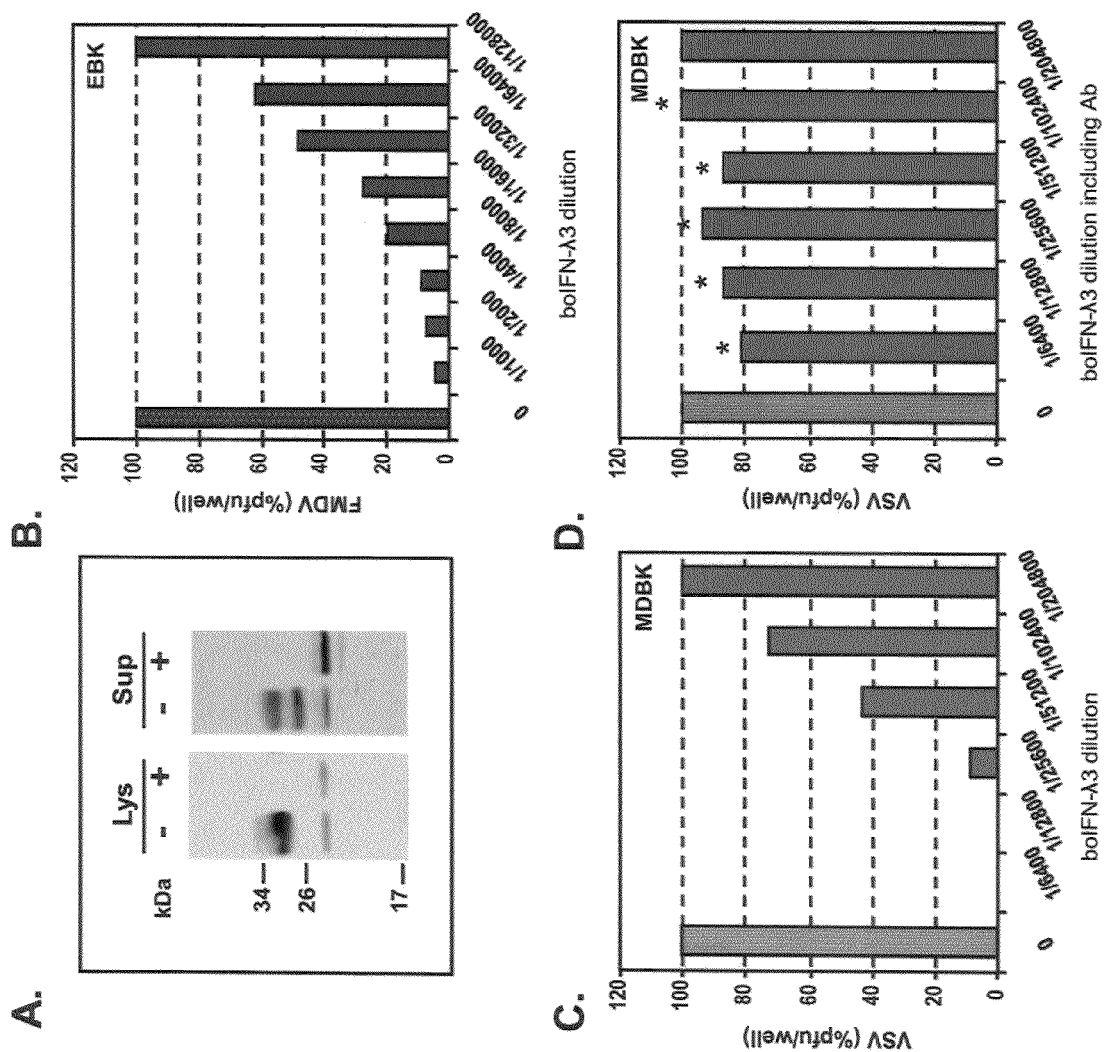
FIGS. 2A-2D depict the characterization of boIFN-λ3 biochemical activity. IBRS2 cells were infected with Ad5-boIFN-λ3 for 24 h in the presence (+) or absence (−) of tunicamycin.
Figure 3:
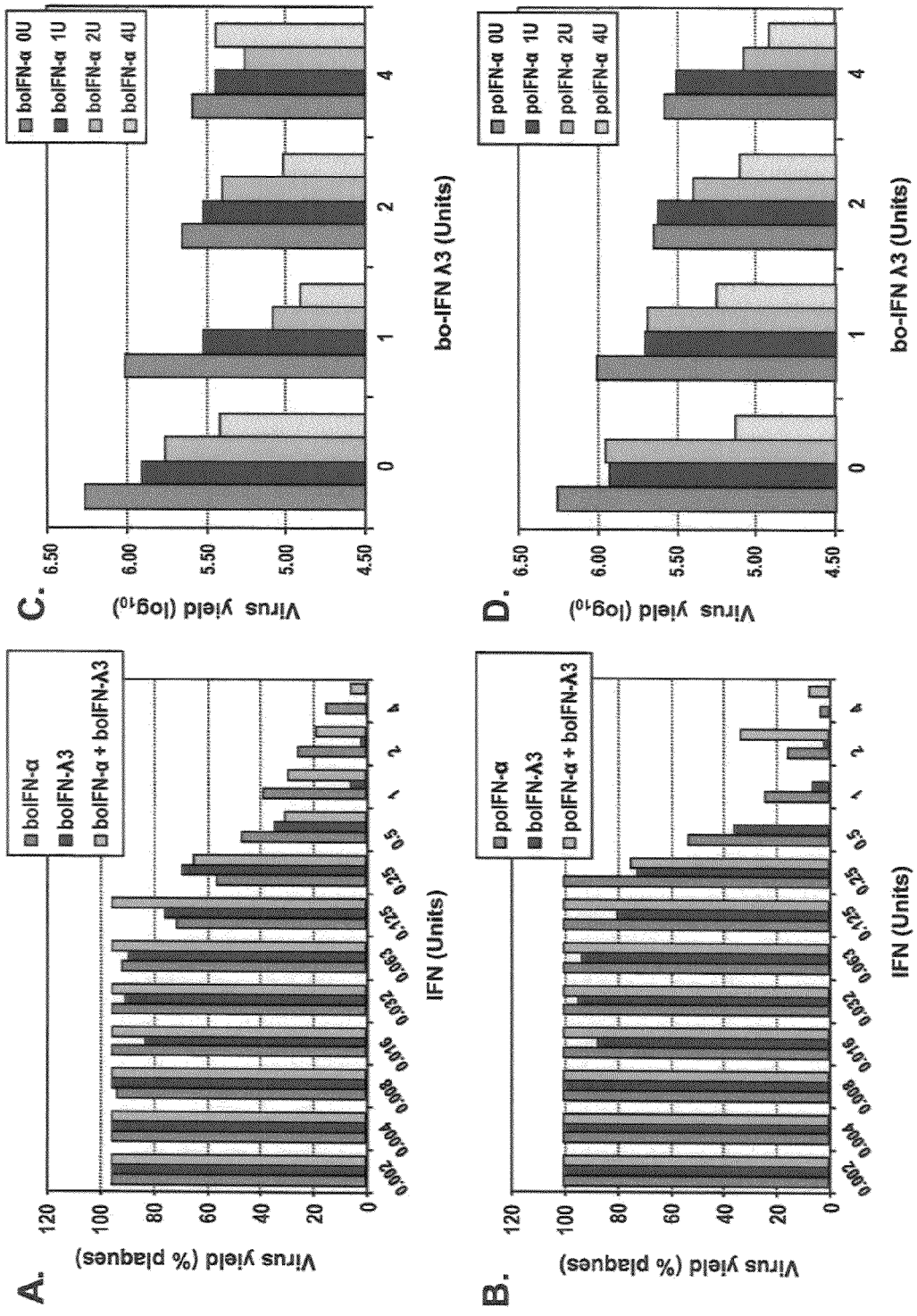
FIGS. 3A-3D depict antiviral activity of boIFN-λ3 against FMDV in combination with boIFN-α or poIFN-α. EBK cells were treated with the indicated concentration of IFNs for 24 h followed by challenge with 100 pfu of FMDV A24. Virus titers were determined by plaque reduction in IFN treated cells relative to mock treated cells (FIGS. 3A and 3B) or virus yield (FIGS. 3C and 3D).

Members of the type III IFN family, also known as IL28A, IL28B and IL29, have been recently identified in several species including human, mouse and swine (Kotenko et al., supra; Sheppard et al., supra). These IFNs are expressed in response to virus infections and mediate the induction of antiviral activities (Kotenko et al., supra; Meager et al. 2005. *Cytokine* 31:109-118; Robek et al., supra; Ank et al. 2006, supra); However, no sequences for type III IFN are available in the published bovine genome. Here we report the identification, cloning and characterization of a member of the bovine (bo) type III IFN family, boIFN-λ3 or bolL28B. Nucleotide and protein sequence analyses indicated that the cloned bovine boIFN-λ3 displays significant homology with respect to previously identified porcine, human and mouse IFN-λ3 sequences, and to the predicted dog, chicken, rat and monkey sequences. By using PCR primers homologous to human sequences, we have amplified the mRNA coding for one member of the bovine type III IFN family, boIFN-λ3 (bolL28B). Cloning of the boIFN-λ3 gene and expression in mammalian cells using an Ad5 vector resulted in the synthesis of an N-linked glycosylated protein of approximately 21-34 kDa that displayed specific antiviral activity against FMDV and vesicular stomatitis virus (VSV) as examined by plaque or virus titer reduction assays in bovine tissue cultures. Additive antiviral activity was detected when bovine cells were treated by a combination of Ad5-boIFN-λ3 and either Ad5-porcine (po)-IFN-α or Ad5-boIFN-α. Analysis of gene expression in cells treated with boIFN-λ3 showed patterns similar to those displayed by treatment with bovine or porcine IFN-α. Inoculation of cattle with Ad5-boIFN-λ3 alone or in combination with Ad5-poIFN-α induced systemic antiviral activity and upregulation of specific gene expression in multiple tissues, particularly in the upper respiratory track. In a first efficacy study, treatment of bovines with Ad5-boIFN-λ3 alone or in combination with Ad5-poIFN-α resulted in delayed and reduced severity of disease after intradermolingual (IDL) challenge with FMDV. Viremia was detected in all experimental animals: however, clinical disease did not appear until 7 days post Ad5-boIFN-λ3 inoculation (6 days post challenge [dpc]) whereas control animals showed clinical signs by 2 dpc. Shedding of FMDV in oral and nasal secretions was also delayed in animals treated with Ad5-boIFN-λ3 as compared to the control group. Finally, in a second efficacy study in which the animals were challenged with FMDV via aerosol, a method that best resembles the natural route of infection, treatment of bovine with Ad5-boIFN-λ3 resulted in protection until 7 dpc. Animals treated with a combination of Ad5-boIFN-λ3 and Ad5-boIFN-α showed delayed of disease and one of the animals in this group never showed clinical signs. On the other hand, animals treated with Ad5-boIFN-α alone started to show clinical signs at 3 dpc as observed in the control group suggesting that Ad5-boIFN-λ3 induced the best protection among all groups.

FMDV is highly sensitive to the actions of type I and type II IFNs in vitro and in vivo (Chinsangaram et al. 1999, 2001, supra; Moraes et al. 2007, supra; Dias et al. 2010, supra); however, since treatment with these IFNs conferred only partial protection in cattle (Wu et al., supra), there is an active interest in developing and testing new antivirals with proven efficacy in this species. Our studies in vitro demonstrated that the identified boIFN-λ3 has antiviral activity against FMDV and VSV and induces the expression of multiple genes: among them, PKR protein kinase-R and OAS1 (2'-5' oligoadenylate synthetase 1b), which have antiviral activity against FMDV (Chinsangaram et al. 1999, supra; de los Santos et al. 2006, supra), and CXCL10 (C—X—C motif chemokine 10) which has been proposed to play a role in immune cell infiltration to the sites of FMDV replication (Diaz-San Segundo et al. 2010, supra). Expression of IFN-stimulated gene 15 (ISG15) was also significantly upregulated in bovine cells treated with IFNs; however, thus far there are no reports describing a role of this gene in controlling FMDV infection. Recently, we have shown that when bovine cells are infected with FMDV, there is an upregulation of ISG15 (Zhu et al. 2010. Virology 404:32-40). Interestingly, the levels of ISG15 are higher when the infection is carried out with an attenuated strain of FMDV, i.e., leaderless virus as compared to wild-type FMDV; however, further work is required to demonstrate a role of this gene in controlling FMD.

To determine if boIFN-λ3 had activity in vivo we performed an initial experiment inoculating one cow each with Ad5 vectors delivering poIFN-α, boIFN-λ3, a combination of both or a control. We chose poIFN-α instead of boIFN-α because in previous experiments we had observed a better antiviral response with poIFN-α despite the species difference (Wu et al. 2003, supra). We inoculated the animals with a relatively high dose of Ad5-vector ($10^{11}$ pfu/animal) to evaluate the response without FMDV challenge. The levels of antiviral activity in serum were rather low considering the high dose of Ad5 used, but significant variation had been previously observed in cattle and swine inoculated with type I IFN alone (Wu et al., supra; Dias et al., supra). Moreover protection has been observed despite low levels of antiviral activity (Dias et al., supra).

Similar to the results in vitro, expression of several genes was induced in the tissues of cows treated with type III IFN. Although most of the analyzed genes were also induced by IFN-α, studies in other animal species suggest that selective expression of the type III IFN receptor in epithelial cells contributes to a better response to this type of IFN and prevents undesired side effects (Ank et al. 2006, supra; Sommereyns et al., supra). For example, Ank et al. (2006, supra) have shown that type III IFN treatment is effective in controlling herpes simplex virus 2 (HSV2) infection in epithelial tissue in vaginal mucosa. It has been reported that upon aerosolization of FMDV, there is a pre-viremic phase and in this period the virus mainly targets epithelial cells of the upper respiratory tract. However, once viremia is established, the virus preferentially infects epithelial cells of the skin and mouth tissues (Pacheco et al. 2010. *The Vet J* 183:46-53; Arzt et al. 2010 *Vet Pathol.* 47:1048-63). Therefore, targeting antivirals to these epithelial cells of the upper respiratory tract should control FMDV replication and spread. Indeed, expression of type III IFN receptors, IL28-Rα and IL10-Rβ, was detected in all analyzed bovine tissues but gene upregulation was highest in the oro-, nasopharynx and palatine tonsil, all tissues present in the upper respiratory tract. The strongest and broadest upregulation in gene expression in response to IFNs treatment was observed for IFN regulatory factor 7 (IRF7), with highest values for the combination treatment of type I and type III IFNs. Expression of IRF7 is per se induced by IFNs and mediates a positive feedback loop that controls the expression of most subtypes of IFN-α and other immunomodulatory molecules (Honda et al. 2005. Nature 434 (7034):772-777; Marie et al. 1998. *EMBO J.* 17:6660-6669). Although we measured the levels of boIFN-α1 by qRTPCR, we did not detect its induction with any treatment (data not shown). However, since there are at least thirteen predicted IFN-α gene sequences within the bovine genome (The Bovine Genome Sequencing and Analysis Consortium et al. 2010, supra), it is possible that other subtypes were induced but not detected with the available reagents. In contrast to the results in cell culture, expression of boIFN-λ3 (IL28B) was induced by Ad5-IFN treatment in most of the analyzed tissues. Thus, this finding suggests that, in vivo in cattle, this cytokine is an IFN-stimulated gene. Overall, upregulation of gene expression in most of the analyzed tissues indicated a systemic response to type I and type III IFN treatments.

Our efficacy studies in cattle showed that boIFN-λ3 displayed an antiviral effect against FMDV. We performed two experiments: 1) We examined the efficacy of treatment with Ad5-boIFN-λ3 alone or in combination with Ad5-poIFN-α based on previous experiments showing that the latter had significant antiviral activity against FMDV in cattle (Wu et al. 2003, supra). We observed that animals treated with Ad5 vectors delivering each IFN alone (Ad5-poIFN-α or Ad5-boIFN-λ3) and challenged by intradermolingual inoculation developed full disease with a clinical score of 5. However, a significant delay was observed in the group treated with Ad5-boIFN-λ3. Further, with the exception of one animal, all animals treated with the combination of Ad5-poIFN-α and Ad5-boIFN-λ3 showed reduced severity and delayed disease, although no significant antiviral activity was detected systemically. It is important to consider that the method of challenge used in this experiment was the most demanding; animals were directly inoculated with FMDV in the tongue epithelia. 2) We also performed an efficacy study by treating bovines with Ad5-boIFN-λ3 alone or in combination with Ad5-boIFN-α and challenging with FMDV by aerosol exposure in a method that best resembles the natural route of exposure to the disease. This method of viral exposure has been previously standardized for different FMDV serotypes (Pacheco et al. 2010 supra). We observed that animals treated with PBS or Ad5 vectors delivering Ad5-boIFN-α at a dose of $1.5 \times 10^{11}$ pfu/animal developed full disease with a clinical score of 5 by 3 days post aerosol exposure to $10^7$ pfu of FMDV O1 Manisa. However, animals that received a combination of Ad5-boIFN-α and Ad5-boIFN-λ3 at a reduced dose of $7 \times 10^{10}$ pfu each/animal showed disease by 5 days post exposure. Remarkably, animals that received Ad5-boIFN-λ3 at a dose of $1.5 \times 10^{11}$ pfu/animal did not show signs of disease for 7 days post exposure. By day 9, only 1 animal of this group had a lesion, a clear sign of reduced severity of disease. By day 12 post FMDV exposure one animal remained disease free, while the other two had low scores, 1 and 3, respectively. These results indicated that administration of Ad5-boIFN-λ3 can protect cattle from FMD when the viral challenge is performed by aerosolization, a method that best resembles the natural route of infection.

Our results show that, as previously reported in other species (Ank et al. 2006, supra; Sommereyns et al. 2008, supra), boIFN-λ3 is involved in establishing an antiviral state in specific bovine tissues such as those present in the upper airways and in the skin, thereby preventing virus spread and the appearance of typical FMD vesicular lesions. Pharmaceutical compositions comprising the boIFN-λ3 gene alone or in combination with porcine or bovine type I (α/β) genes are an effective antiviral strategy against FMDV to limit the rate, degree, and severity of FMD.

Production and manipulation of the isolated polynucleotide molecules described herein are within the skill in the art and can be carried out according to recombinant techniques described, among other places, in Sambrook et al. 1989. *Molecular Cloning: A Laboratory Manual*, 2d ed., Cold Spring Harbor Laboratory Press, Cold Spring Harbor, N.Y. and Innis et al. (eds). 1995. *PCR Strategies*, Academic Press, Inc., San Diego, which are incorporated herein by reference.

The subject invention provides vectors comprising isolated polynucleotide molecules comprising genetically modified nucleic acid sequences that encode bovine IFN-λ3, porcine IFN-α/β, bovine IFN-α/β, and FMD antigen.

For purposes of the present invention, two DNA sequences are substantially homologous when at least 80% (preferably at least 85% and most preferably 90%) of the nucleotides match over the defined length of the sequence using algorithms such as CLUSTAL or PILEUP. Sequences that are substantially homologous can be identified in a Southern hybridization experiment under stringent conditions as is known in the art. See, for example, Sambrook et al. supra. Sambrook et al. describe highly stringent conditions as a hybridization temperature 5-10° C. below the $T_m$ of a perfectly matched target and probe; thus, sequences that are "substantially homologous" would hybridize under such conditions.

As used herein, "substantially similar" refers to nucleic acid fragments wherein changes in one or more nucleotide bases results in substitution of one or more amino acids, but do not affect the functional properties of the polypeptide encoded by the nucleotide sequence. "Substantially similar" also refers to modifications of the nucleic acid fragments of the instant invention such as deletion or insertion of nucleotides that do not substantially affect the functional properties of the resulting transcript. It is therefore understood that the invention encompasses more than the specific exemplary nucleotide or amino acid sequences and includes functional equivalents thereof. Alterations in a nucleic acid fragment that result in the production of a chemically equivalent amino acid at a given site, but do not affect the functional properties of the encoded polypeptide, are well known in the art. Thus, a codon for the amino acid alanine, a hydrophobic amino acid, may be substituted by a codon encoding another less hydrophobic residue, such as glycine, or a more hydrophobic residue, such as valine, leucine, or isoleucine. Similarly, changes which result in substitution of one negatively charged residue for another, such as aspartic acid for glutamic acid, or one positively charged residue for another, such as lysine for arginine, can also be expected to produce a functionally equivalent product. Nucleotide changes which result in alteration of the N-terminal and C-terminal portions of the polypeptide molecule would also not be expected to alter the activity of the polypeptide. Each of the proposed modifications is well within the routine skill in the art, as is determination of retention of biological activity of the encoded products. A method of selecting an isolated polynucleotide that affects the level of expression of a polypeptide in a virus or in a host cell (eukaryotic, such as plant, yeast, fungi, or algae; prokaryotic, such as bacteria) may comprise the steps of: constructing an isolated polynucleotide of the present invention or an isolated chimeric gene of the present invention; introducing the isolated polynucleotide or the isolated chimeric gene into a host cell; measuring the level of a polypeptide in the host cell containing the isolated polynucleotide; and comparing the level of a polypeptide in the host cell containing the isolated polynucleotide with the level of a polypeptide in a host cell that does not contain the isolated polynucleotide.

Moreover, substantially similar nucleic acid fragments may also be characterized by their ability to hybridize. Estimates of such homology are provided by either DNA-DNA or DNA-RNA hybridization under conditions of stringency as is well understood by those skilled in the art (1985. *Nucleic Acid Hybridization*, Hames and Higgins, Eds., IRL Press, Oxford, U.K.). Stringency conditions can be adjusted to screen for moderately similar fragments, such as homologous sequences from distantly related organisms, to highly similar fragments, such as genes that duplicate functional enzymes from closely related organisms.

Substantially similar nucleic acid fragments of the instant invention may also be characterized by the percent identity of the amino acid sequences that they encode to the amino acid sequences disclosed herein, as determined by algorithms commonly employed by those skilled in this art.

Methods of alignment of sequences for comparison are well known in the art. Thus, the determination of percent identity between any two sequences can be accomplished using a mathematical algorithm. Non-limiting examples of such mathematical algorithms are the algorithm of Myers and Miller (1988. *CABIOS* 4:11-17), the local homology algorithm of Smith et al. (1981. *Adv. Appl. Math.* 2:482); the homology alignment algorithm of Needleman and Wunsch (1970. *J. Mol. Biol.* 48:443-453); the search-for-similarity-method of Pearson and Lipman (1988. *Proc. Natl. Acad. Sci.* 85:2444-2448; the algorithm of Karlin and Altschul (1990. *Proc. Natl. Acad. Sci. USA* 87:2264), modified as in Karlin and Altschul (1993. *Proc. Natl. Acad. Sci. USA* 90:5873-5877).

Computer implementations of these mathematical algorithms can be utilized for comparison of sequences to determine sequence identity. Such implementations include, but are not limited to: CLUSTAL in the PC/Gene program (available from Intelligenetics, Mountain View, Calif.); the ALIGN program (Version 2.0) and GAP, BESTFIT, BLAST, FASTA, and TFASTA in the Wisconsin Genetics Software Package, Version 8 (available from Genetics Computer Group (GCG), 575 Science Drive, Madison, Wis., USA). Alignments using these programs can be performed using the default parameters.

As used herein, "sequence identity" or "identity" in the context of two nucleic acid or polypeptide sequences makes reference to the residues in the two sequences that are the same when aligned for maximum correspondence over a specified comparison window. When percentage of sequence identity is used in reference to proteins, it is recognized that residue positions which are not identical often differ by conservative amino acid substitutions, where amino acid residues are substituted for other amino acid residues with similar chemical properties (e.g., charge or hydrophobicity) and therefore do not change the functional properties of the molecule.

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

As used herein, "reference sequence" is a defined sequence used as a basis for sequence comparison. A reference sequence may be a subset or the entirety of a specified sequence; for example, as a segment of a full-length cDNA or gene sequence, or the complete cDNA or gene sequence.

The term "substantial identity" of polynucleotide sequences means that a polynucleotide comprises a sequence that has at least 80% sequence identity, preferably at least 85%, more preferably at least 90%, most preferably at least 95% sequence identity compared to a reference sequence using one of the alignment programs described using standard parameters. One of skill in the art will recognize that these values can be appropriately adjusted to determine corresponding identity of proteins encoded by two nucleotide sequences by taking into account codon degeneracy, amino acid similarity, reading frame positioning, and the like. Substantial identity of amino acid sequences for these purposes normally means sequence identity of at least 80%, preferably at least 85%, more preferably at least 90%, and most preferably at least 95%. Preferably, optimal alignment is conducted using the homology alignment algorithm of Needleman et al. (1970. *J. Mol. Biol.* 48:443).

Another indication that nucleotide sequences are substantially identical is if two molecules hybridize to each other under stringent conditions. Generally, stringent conditions are selected to be about 5° C. lower than the thermal melting point (Tm) for the specific sequence at a defined ionic strength and pH. However, stringent conditions encompass temperatures in the range of about 1° C. to about 20° C., depending upon the desired degree of stringency as otherwise qualified herein.

A "substantial portion" of an amino acid or nucleotide sequence comprises an amino acid or a nucleotide sequence that is sufficient to afford putative identification of the protein or gene that the amino acid or nucleotide sequence comprises. Amino acid and nucleotide sequences can be evaluated either manually by one skilled in the art, or by using computer-based sequence comparison and identification tools that employ algorithms such as BLAST. In general, a sequence of ten or more contiguous amino acids or thirty or more contiguous nucleotides is necessary in order to putatively identify a polypeptide or nucleic acid sequence as homologous to a known protein or gene. Moreover, with respect to nucleotide sequences, gene-specific oligonucleotide probes comprising 30 or more contiguous nucleotides may be used in sequence-dependent methods of gene identification and isolation. In addition, short oligonucleotides of 12 or more nucleotides may be use as amplification primers in PCR in order to obtain a particular nucleic acid fragment comprising the primers. Accordingly, a "substantial portion" of a nucleotide sequence comprises a nucleotide sequence that will afford specific identification and/or isolation of a nucleic acid fragment comprising the sequence. The skilled artisan, having the benefit of the sequences as reported herein, may now use all or a substantial portion of the disclosed sequences for purposes known to those skilled in this art. Accordingly, the instant invention comprises the complete sequences as reported in the accompanying Sequence Listing, as well as substantial portions at those sequences as defined above.

By "variants" substantially similar sequences are intended. For nucleotide sequences, conservative variants include those sequences that, because of the degeneracy of the genetic code, encode the amino acid sequence of the IFN-λ3 and IFN-α/β of the invention. Naturally occurring allelic variants such as these can be identified with the use of well-known molecular biology techniques, as, for example, with polymerase chain reaction (PCR), a technique used for the amplification of specific DNA segments. Generally, variants of a particular nucleotide sequence of the invention will have generally at least about 90%, preferably at least about 95% and more preferably at least about 98% sequence identity to that particular nucleotide sequence as determined by sequence alignment programs described elsewhere herein.

By "variant protein" a protein derived from the native protein by deletion (so-called truncation) or addition of one or more amino acids to the N-terminal and/or C-terminal end of the native protein; deletion or addition of one or more amino acids at one or more sites in the native protein; or substitution of one or more amino acids at one or more sites in the native protein is intended. Variant proteins encompassed by the present invention are biologically active, that is they possess the desired biological activity, that is, IFN-λ3 and type I IFN activity as described herein. Such variants may result from, for example, genetic polymorphism or from human manipulation. Biologically active variants of the IFN-λ3 and type I IFN of the invention will have at least about 90%, preferably at least about 95%, and more preferably at least about 98% sequence identity to the amino acid sequence for the native protein as determined by sequence alignment programs described elsewhere herein. A biologically active variant of a protein of the invention may differ from that protein by as few as 1-15 amino acid residues, or even 1 amino acid residue.

The polypeptides of the invention may be altered in various ways including amino acid substitutions, deletions, truncations, and insertions. Novel proteins having properties of interest may be created by combining elements and fragments of proteins of the present invention, as well as with other proteins. Methods for such manipulations are generally known in the art. Thus, the genes and nucleotide sequences of the invention include both the naturally occurring sequences as well as mutant forms. Likewise, the proteins of the invention encompass naturally occurring proteins as well as variations and modified forms thereof. Such variants will continue to possess the desired IFN-λ3 and type I IFN activity. Obviously, the mutations that will be made in the DNA encoding the variant must not place the sequence out of reading frame and preferably will not create complementary regions that could produce secondary mRNA structure.

The deletions, insertions, and substitutions of the protein sequences encompassed herein are not expected to produce radical changes in the characteristics of the protein. However, when it is difficult to predict the exact effect of the substitution, deletion, or insertion in advance of doing so, one skilled in the art will appreciate that the effect will be evaluated by routine screening assays where the effects of IFN-λ3 and type I IFN can be observed.

"Codon degeneracy" refers to divergence in the genetic code permitting variation of the nucleotide sequence without affecting the amino acid sequence of an encoded polypeptide. Accordingly, the instant invention relates to any nucleic acid fragment comprising a nucleotide sequence that encodes all or a substantial portion of the amino acid sequences set forth herein.

It is furthermore to be understood that the isolated polynucleotide molecules and the isolated RNA molecules of the present invention include both synthetic molecules and molecules obtained through recombinant techniques, such as by in vitro cloning and transcription.

As used herein, the term "FMD" encompasses disease symptoms in swine, cows, sheep, and goats caused by a FMDV infection. Examples of such symptoms include, but are not limited to: fever, lameness and vesicular lesions on the feet, tongue, snout and teats.

The terms "foot and mouth disease virus" and "FMDV", as used herein, unless otherwise indicated, mean any strain of FMD viruses.

The term "open reading frame", or "ORF", as used herein, means the minimal nucleotide sequence required to encode a particular FMDV protein without an intervening stop codon.

Terms such as "suitable host cell" and "appropriate host cell", unless otherwise indicated, refer to cells into which RNA molecules (or isolated polynucleotide molecules or viral vectors comprising DNA sequences encoding such RNA molecules) of the present invention can be transformed or transfected. "Suitable host cells" for transfection with such RNA molecules, isolated polynucleotide molecules, or viral vectors, include mammalian, particularly porcine, bovine, caprine, and ovine cells.

A "functional virion" is a virus particle that is able to enter a cell capable of hosting a FMDV, and express genes of its particular RNA genome (either an unmodified genome or a genetically modified genome as described herein) within the cell. Cells capable of hosting a FMDV include, for example, baby hamster kidney cells (e.g., BHK-21 cells), swine kidney cells (e.g., IBRS-2 cells) and bovine kidney cells (e.g., embryonic bovine kidney—EBK cells- or LF-BK cells). Other cells may also serve as suitable host cells for FMD virions.

The term "immune response" for purposes of this invention means the production of antiviral molecules such as cytokines, e.g. interferons, chemokines, etc and/or antibodies and/or cells (such as T lymphocytes) that are directed against, or assist in the decomposition or inhibition of, a particular infectious agent such as a virus or an antigenic epitope or particular antigenic epitopes. The phrases "an effective immunoprotective response", "immunoprotection", and like terms, for purposes of the present invention, mean an immune response that is directed against an infectious agent such a virus as a whole and/or one or more antigenic epitopes of a pathogen so as to protect against infection by the pathogen in a treated animal. For purposes of the present invention, protection against infection by a pathogen includes not only the absolute prevention of infection, but also any detectable reduction in the degree or rate of infection by a pathogen, or any detectable reduction in the severity of the disease or any symptom or condition resulting from infection by the pathogen in the vaccinated animal as compared to an unvaccinated infected animal. An effective immunoprotective response can be induced in animals that have not previously been infected with the pathogen and/or are not infected with the pathogen at the time of treatment. An effective immunoprotective response can also be induced in an animal already infected with the pathogen at the time of treatment.

An "antigenic epitope" is, unless otherwise indicated, a molecule that is able to elicit an immune response in a particular animal or species. Antigenic epitopes are proteinaceous molecules, i.e. polypeptide sequences, optionally comprising non-protein groups such as carbohydrate moieties and/or lipid moieties.

In a further preferred embodiment, an antigenic epitope of the genetically modified FMDV of the present invention is a detectable antigenic epitope. Such isolated polynucleotide molecules and the FMD viruses they encode are useful, inter alia, for studying FMDV infections in cows, swine, goats, and sheep, determining successfully vaccinated cows, swine, goats, and sheep, and/or for distinguishing said vaccinated animals from cows, swine, goats, and sheep infected by a wild-type FMDV. Preferably, such isolated polynucleotide molecules further contain one or more mutations that genetically disable the encoded FMDV in its ability to produce FMD, and more preferably are able to elicit an effective immunoprotective response in a porcine animal against infection by a FMDV.

Antigenic epitopes that are detectable, and the sequences that encode them, are known in the art. Techniques for detecting such antigenic epitopes are also known in the art and include serological detection of antibody specific to the heterologous antigenic epitope by means of, for example, Western blot, ELISA, or fluorescently labeled antibodies capable of binding to the antibodies specific to the heterologous antigenic epitope. Techniques for serological detection useful in practicing the present invention can be found in texts recognized in the art, such as Coligan, J. E., et al. (eds), 1998, *Current Protocols in Immunology*, John Willey & Sons, Inc., which is hereby incorporated by reference in its entirety. Alternatively, the antigenic epitope itself can be detected by, for example, contacting samples that potentially comprise the antigenic epitope with fluorescently-labeled antibodies or radioactively-labeled antibodies that specifically bind to the antigenic epitopes.

Biotherapeutic compositions and/or vaccines of the present invention can be formulated following accepted convention to include acceptable carriers for animals, including humans (if applicable), such as standard buffers, stabilizers, diluents, preservatives, and/or solubilizers, and can also be formulated to facilitate sustained release. Diluents include water, saline, dextrose, ethanol, glycerol, and the like. Additives for isotonicity include sodium chloride, dextrose, mannitol, sorbitol, and lactose, among others. Stabilizers include albumin, among others. Other suitable vaccine vehicles and additives, including those that are particularly useful in formulating modified live vaccines, are known or will be apparent to those skilled in the art. See, e.g., *Remington's Pharmaceutical Science*, 18th ed., 1990, Mack Publishing, which is incorporated herein by reference.

Biotherapeutic compositions and/or vaccines of the present invention comprise vectors comprising genes encoding IFN-λ3 or a combination of IFN 3 and type I IFN or a combination of IFN-λ3 with FMD antigen or a combination of IFN-λ3 with type I IFN and FMD antigen. Adjuvants can be used in the vaccine of the present invention and can include, for example, the RIBI adjuvant system (Ribi Inc., Hamilton, Mont.), alum, mineral gels such as aluminum hydroxide gel, oil-in-water emulsions, water-in-oil emulsions such as, e.g., Freund's complete and incomplete adjuvants, Block copolymer (CytRx, Atlanta Ga.), QS-21 (Cambridge Biotech Inc., Cambridge Mass.), SAF-M (Chiron, Emeryville Calif.), AMPHIGEN® adjuvant, saponin, Quil A or other saponin fraction, monophosphoryl lipid A, and Avridine lipid-amine adjuvant. Non-limiting examples of oil-in-water emulsions useful in the vaccine of the invention include modified SEAM62 and SEAM 1/2 formulations. Modified SEAM62 is an oil-in-water emulsion containing 5% (v/v) squalene (Sigma), 1% (v/v) SPAN® 85 detergent (ICI Surfactants), 0.7% (v/v) TWEEN® 80 detergent (ICI Surfactants), 2.5% (v/v) ethanol, 200 µg/ml Quil A, 100 µg/ml cholesterol, and 0.5% (v/v) lecithin. Modified SEAM 1/2 is an oil-in-water emulsion comprising 5% (v/v) squalene, 1% (v/v) SPAN® 85 detergent, 0.7% (v/v) Tween 80 detergent, 2.5% (v/v) ethanol, and 100 µg/ml Quil A. Other immunomodulatory agents that can be included in the vaccine include, e.g., one or more interleukins, other interferons, or other known cytokines.

An effective amount of any of the above-described biotherapeutic compositions/immunomodulators/vaccines can be determined by conventional means, starting with a low dose of virus, plasmid or viral vector, and then increasing the dosage while monitoring the effects. An effective amount may be obtained after a single administration of the biotherapeutic compositions/immunomodulators/vaccines or after multiple administrations of the biotherapeutics/immunomodulators/vaccines. Known factors can be taken into consideration when determining an optimal dose per animal. These include the species, size, age and general condition of the animal, the presence of other drugs in the animal, and the like. The actual dosage is preferably chosen after consideration of the results from other animal studies.

The effective dose amount of virus, infectious RNA molecule, plasmid, or viral vector, of the present invention can be determined using known techniques, taking into account factors that can be determined by one of ordinary skill in the art such as the weight of the animal to be vaccinated.

EXAMPLES

Having now generally described this invention, the same will be better understood by reference to certain specific examples, which are included herein only to further illustrate the invention and are not intended to limit the scope of the invention as defined by the claims.

Example 1

Cell Lines and Viruses

Human 293 cells (ATCC CRL-1573) were used to generate and propagate recombinant adenovirus. Embryonic bovine kidney (EBK) cells and porcine kidney cells (IB-R52) were obtained from the Foreign Animal Disease Diagnostic Laboratory (APHIS) at Plum Island Animal Disease Center (PI-ADC), Greenport, N.Y. Madin-Darby bovine kidney cells (MDBK, ATCC CCL-22) were purchased from the American Type Culture Collection (ATCC, Rockville, Md.). All cells were maintained in Eagle's minimal essential medium (EMEM) containing either 10% calf serum or 10% fetal bovine serum (FBS) supplemented with antibiotics. Baby hamster kidney cells (BHK-21, ATCC CCL-10) were used to propagate and titrate FMDV. These cells were maintained in EMEM containing 10% calf serum and 10% tryptose phosphate broth supplemented with antibiotics. FMDV subtype A12 was generated from the full-length infectious clone pRMC35 and used for the biologic assay of IFN. For cattle challenge, FMDV A24 Cruzeiro (a gift of Dr. Tanuri, Federal University of Rio de Janeiro, Brazil) was obtained from the vesicular lesions of an FMDV A24-infected pig. The bovine infectious dose ($BID_{50}$) was determined by standard methods (Henderson, W. M. 1949. Report Series Agricultural Research Council, London, Vol. 8. Her Majesty's Stationery Office; Henderson, W. M. 1952. *J. Hyg. Camb.* 50: 182-194). Vesicular stomatitis virus (VSV) serotype New Jersey was provided by APHIS at PIADC.

Example 2

Identification, Cloning and Expression of boIFN-λ3

RNA was isolated from EBK cells infected with an attenuated FMDV serotype A12 strain lacking the leader protein coding region (leaderless virus; Piccone et al. 1995. *J. Virol.* 69: 5376-82) at MOI 1 for 6 h, and using an RNeasy mini kit (Qiagen, Valencia, Calif.) following the manufacturer's directions. Approximately 1 µg of RNA was treated with DNase I (Sigma, St. Louis, Mo.) and was used to synthesize cDNA with M-MLV reverse transcriptase (Invitrogen) and random hexamers following the manufacturer's directions. Two oligonucleotides: 5' ATCGAT ATGGCCCCGGGCTG CACGCT 3' (FW) (SEQ ID NO:12) and 5' TCTAGA TTAGA-CACACTGGTCTCCGCT GGC 3' (RW) (SEQ ID NO:13) containing ClaI and XbaI restriction sites respectively were designed to amplify the putative IL28B sequence using the prepared bovine cDNA as template. The amplified PCR fragment was digested with ClaI and XbaI and cloned into the plasmid pAd5-Blue (Moraes et al. 2001. *Bio Techniques* 31: 1050-1056) for expression in mammalian systems. The sequence of the amplified fragment (boIFN-λ3 was confirmed by standard DNA sequencing in an ABI 3730 XL system (Applied Biosystems, Foster City, Calif.).

Recombinant Ad5 viruses including Ad5-boIFN-λ3, Ad5-poIFN-α and Ad5-Blue were produced by transfection of 293 cells with the respective PacI-digested pAd5 plasmids. Viruses were plaque-isolated, propagated in 293 cells and purified by CsCl gradient centrifugation. Viral titer was determined by the method of tissue culture infectious dose 50 ($TCID_{50}$) and converted to plaque-forming units (pfu)/ml.

To analyze the protein expressed by the Ad5-boIFN-λ3, IBRS2 cells were infected with the Ad5-boIFN-λ3 vector and cellular extracts and supernatants were subjected to SDS PAGE followed by Western blot analysis. A polyclonal antibody was obtained by inoculation of rabbits with the same Ad5-boIFN-λ3 vector. When indicated, tunicamycin (5 µg/ml) was added during the infection to examine for the presence of N-linked glycosylation.

Figure 1A:
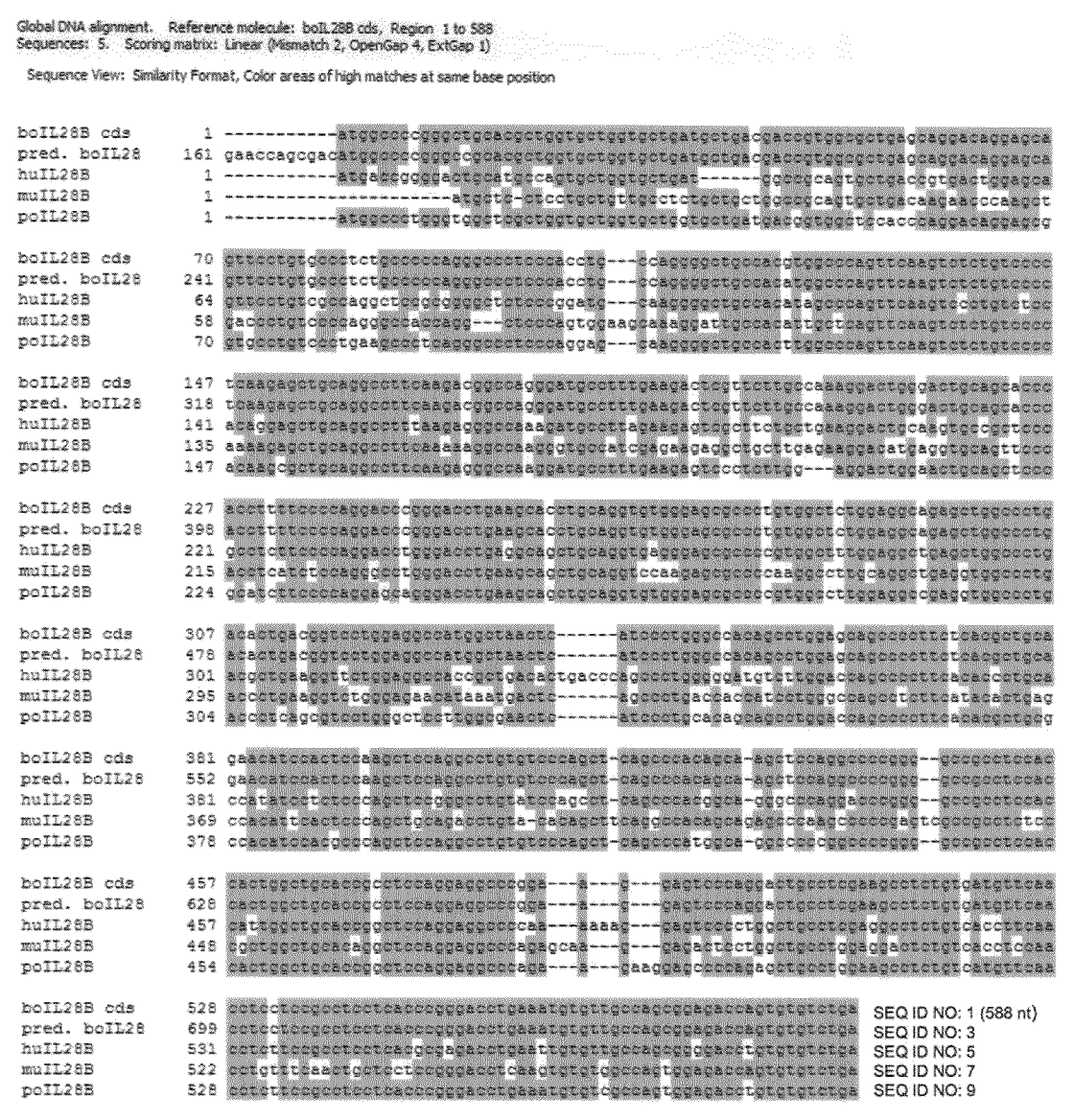

In previous studies we have described the design of a DNA microarray used to evaluate transcription profiles of bovine cells infected with FMDV (Zhu et al. 2010, supra). Although bovine type III IFNs sequences had not been identified, we included in the microarray several probes with sequence homology to human type III IFNs. Interestingly, we observed that upon FMDV infection, there was significant up-regulation of the mRNA detected by the homologous IFN-λ3 probe. Therefore to better understand if type III IFN plays any role in controlling FMDV infection, we intended to amplify the full length coding sequence of boIFN-λ3 by RT-PCR of mRNA extracted from primary embryonic bovine kidney cells. We identified a 818 nt cDNA fragment (SEQ ID NO: 11) containing the sequence of boIFN-λ3 (boIL28B). The coding region (nt 99 to nt 683) is a fragment of 585 nucleotides (SEQ ID NO:1 [588 nucleotides minus the TGA stop codon]; FIG. 1A) corresponding to a full length open reading frame of 195 amino acids (SEQ ID NO:2) with significant sequence homology to the previously identified IL28B sequences in *Sus scrofa* (po) (NM_001166490), *Homo sapiens* (hu) (NM_172139) *Mus musculus* (mu) (NM_177396) and an IL28B-predicted *Bos Taurus* (bo) sequence recently deposited in GenBank (XM_002695050) (FIG. 1A, 1B). The closest homology was observed with respect to the *Sus scrofa* counterpart with values of 85% for the DNA and 76% for the protein sequences (FIG. 1C, 1D). When considering the predicted bo IL28B full sequence (759 bp or 252 aa) a homology of 77% for the DNA and 76% for the protein were determined, however if a modified version of this sequence—deleted 171 bp from the N terminus—is used, there is a homology of 99% at the DNA and protein levels (data not shown). Homologies between 70-79% for the DNA and 56 to 66% for the protein sequences were observed when the boIFN-λ3 sequence was compared to huIFN-λ3 and muIFN-λ3, respectively (FIG. 1C, 1D). The identified sequence encoded for a protein of MW=21587.6 with a pI of 8.20 that contained a predicted signal peptide for secretion between amino acids 1 and 24 (Bendtsen et al. 2004. *J. Mol. Biol.* 340:783-795) and a putative N-linked glycosylation sequence between amino acids 112 and 115 (Gupta, Jung and Brunak. 2004. Retrieved from the Internet: <URL: cbs.d-tu.dk/services/NetNGlyc 1.0 Server).

Example 3

Antiviral Activity of boIFN-λ3

Antiviral activity was evaluated in plasma samples and nasal and oral swabs as described elsewhere (Chinsangaram et al. 2001, supra). Briefly, serial 2-fold dilutions of samples (ranging from 1/25 to 1/6,400), obtained at −1, 0 and 1 dpc, were incubated on MDBK cells. Twenty-four hours later, supernatants were removed, and the cells were infected for 1 h with approximately 100 PFU/ml of VSV. Cells were then overlaid with gum tragacanth and incubated for 48 h. Plaques were visualized by staining with crystal violet. Antiviral activity was determined as the reciprocal of the highest supernatant dilution that resulted in a 50% reduction in the number of plaques relative to the number of plaques in the untreated infected cells and results were expressed as units of antiviral activity/ml of sample.

In order to corroborate the predicted biochemical properties and determine if the identified boIFN-λ3 sequence encoded for a biologically active IFN product, we expressed the protein using an Ad5 vector containing the cytomegalovirus (CMV) immediate early promoter to drive transcription of the gene (Moraes et al. 2001, supra). Porcine IBRS-2 cells, which do not express endogenous type I IFNs (Chinsangaram et al. 2001, supra), were infected with the Ad5-boIFN-λ3 vector and protein expression was analyzed in cell extracts and supernatants. A secreted protein with multiple bands between 21 and 34 kDa was detected in the supernatant of infected cells by western blot analysis using a specific rabbit polyclonal antibody obtained in our laboratory. Addition of tunicamycin, an inhibitor of N-linked glycosylation, to the Ad5-boIFN-λ3 infected IBRS-2 cells, resulted in a secreted protein with a discrete MW of approximately 21 kDa indicating that boIFN-λ3 protein was glycosylated at Asn residues (FIG. 2A).

The biological activity of the expressed boIFN-λ3 protein was tested in EBK and MDBK cells which were pretreated for 24 h with supernatants (filtered to remove Ad5 vector) from Ad5-boIFN-λ3-infected IBRS2 cells. Twenty four hours later, EBK cells were challenged with FMDV and MDBK cells with VSV. FIG. 2B shows that the supernatants from Ad5-boIFN-λ3 infected-IBRS2 cells contained between 16,000 and 32,000 U/ml of antiviral activity against FMDV. A stronger response, 51,200 to 102,200 U/ml, was observed when the same supernatant was tested in MDBK cells challenged with VSV (FIG. 2C). The specificity of the response was determined by incubating the same supernatants with rabbit anti-boIFN-λ3 serum prior to the assay. Most of the antiviral activity, 80 to 90%, was neutralized by addition of the specific antibody (FIG. 2D). No background antiviral activity was detected in supernatants from uninfected or Ad5-Blue infected porcine IBRS2 cells (data not shown). These results indicated that the expressed boIFN-λ3 displays potent antiviral activity in bovine epithelial cells.

It has been reported that although type I and type III IFN bind distinct specific receptors, they induce similar cellular responses (Stark et al. 1998. *Annu. Rev. Biochem.* 67:227-264; Sheppard et al., supra; Kotenko et al., supra; Sommereyns et al., supra). We therefore assayed the antiviral activity of MDBK or EBK cells treated with boIFN-α and boIFN-λ3 or a combination of both IFNs, against VSV and FMDV. We also incubated the cells with poIFN-α, which displays antiviral activity in bovine cells (Wu et al., supra). FIGS. 3A and 3B show the results of a plaque reduction assay in MDBK cells treated with increasing concentrations of boIFN-α, boIFN-λ3, or poIFN-α alone, or combinations of boIFN-α and boIFN-λ3 or poIFN-α and boIFN-λ3, all challenged with VSV. A plaque reduction of approximately 58-64% was observed when cells were treated with 0.5 U of either IFN alone or a combination of 0.25 U each. The same pattern was more or less reproducible for all tested combinations. Similar to our previous results, a dose response effect was evident with each IFN but with this assay, no additive or synergistic response was detected when the total units of the combination treatment equaled the number of units of each IFN alone.

A similar bioassay was used to measure virus yield instead of plaque reduction. EBK cells were incubated with media containing different concentrations and combinations poIFN-α, boIFN-α and boIFN-λ3. Twenty four hours after treatment the cells were challenged with FMDV at MOI 1 and virus yield was measured on BHK-21 cells at 8 hpi. As shown in FIG. 3C, treatment with boIFN-λ3 alone (0 to 4 U) reduced the viral titer from 6.26 to 5.50 $\log_{10}$ pfu/ml. Similarly, treatment with boIFN-α (0 to 4 U) reduced the titer from 6.26 to 5.41 $\log_{10}$ pfu/ml and treatment with poIFN-α from 6.26 to 5.14 $\log_{10}$ pfu/ml. Combination treatment of boIFN-λ3 with boIFN-α or poIFN-α showed slightly enhanced activity. For example when 1 U of boIFN-λ3 was added to 2 U of boIFN-α the titer was reduced from 5.76 to 5.08 $\log_{10}$ pfu/ml. Combination of 1 U of boIFN-λ3 with 2 U of poIFN-α reduced the titer from 5.95 to 5.40 $\log_{10}$ pfu/ml (FIG. 3D). No synergistic effect was observed for any of the combination IFN concentrations tested suggesting that type I and type III IFN activate the same pathways to exert antiviral activity in bovine cells.

Example 4

Genes Induced by boIFN-λ3 in Bovine Cells

A quantitative real-time reverse transcription-PCR (RT-PCR) assay was standardized and used to evaluate the mRNA levels of multiple genes in monolayers of EBK cells or bovine tissues exposed to different IFNs. RNA and cDNA were prepared as described above. An aliquot (1/40) of the cDNA was used as template for real-time PCR using TaqMan Universal PCR Master Mix (Applied Biosystems). Primers and TaqMan minor groove binding (MGB) probes were designed with Primer Express™ software v.1.5 (Applied Biosystems). Forward and reverse primers were purchased from Invitrogen (Carlsbad, Calif.) and the FAM-labeled TaqMan MGB probes from Applied Biosystems. Bovine glyceraldehyde 3-phosphate dehydrogenase (GAPDH) was used as internal control to normalize the values for each sample. The sequences for the primers and probes (SEQ ID NOs: 14-61) are listed in Tables 1 and 2. Reactions were performed in an ABI Prism 7900 Sequence detection system (Applied Biosystems).

To better understand the mechanism of antiviral activity elicited by boIFN-λ3 in bovine cells, we measured the levels of RNA for IFNs and several IFN-stimulated genes whose expression has been shown to be up-regulated by type III IFN in other species. For the analysis of gene expression we focused on IFN-α, β, and IFN-stimulated genes including IFN-λ3, chemokines CCL2, CCL3, CCL20, CXCL10, activators of the IFN pathway such as IRF7 and MDA5 (melanoma differentiation-associated gene 5) and some genes with known antiviral activity, ISG15, Mx1 (myxovirus resistance 1), OAS1 and PKR. We also measured the expression of type III IFN receptors, IL28-Rα and IL10-Rβ. A dose response effect was observed for several genes when the cells were incubated with each IFN independently (FIG. 4). Relative induction of IRF7 increased from 4.6 to 9.8 when 5 to 100 U of boIFN-λ3 were added, from 8.4 to 15.1 when 5 to 100 U of poIFN-α were added and from 3.6 to 7.2 when 5 to 100 U of boIFN-α were added. However, we could not detect any additive or synergistic effect when boIFN-λ3 was used in combination with poIFN-α or boIFN-α. From the analysis we concluded that 50 U of each IFN was enough to reach the saturation level since almost no difference in the response was observed when we added 100 U IFN. In addition, we observed that 5 U of boIFN-λ3 in combination with 5 U of poIFN-α induced a similar response as 10 U of boIFN-λ3. Treatment with 5 U of boIFN-λ3 in combination with 5 U of boIFN-α induced a similar response as 5 U of boIFN-α alone. Analysis of the expression of the type III IFN specific receptors (IL28B-Rα and IL10-Rβ) showed considerable basal levels of RNA with ct values of 24-28 as compared to ct values of 20-21 for the housekeeping gene GAPDH, in samples containing 5 ng of total RNA. Expression of such levels of IL28B-Rα and IL10-Rβ is consistent with the sensitivity of these cells to type III IFN. No induction of type I or type III IFN mRNA was observed in these cells after treatment with boIFN-λ3, boIFN-α, or poIFN-α.

TABLE 1

Bovine oligonucleotide primer sequences for real-time RT-PCR.

| Gene | Accession # | Forward Primer | Reverse Primer | SEQ ID # FR | - RP |
|---|---|---|---|---|---|
| CCL2 | EU276059 | GCTACTCACAGTAGCTGCCTTCAG-30 | GCGACTTGGGAGTTAATTGCA-98 | 14 | 30 |
| CCL3 | AY077840 | AGCCAGGTCTTCTCGGCAC-124 | AGAAGCAGCAGGCCGTTG-178 | 15 | 31 |
| CCL20 | NM_174263 | CCAGTATTCTTGTGGGCTTCACA-166 | GGTGTAAAAGACAACTGCATTGATG-239 | 16 | 32 |
| CXCL10 | EU276062 | GTCATTCCTGCAAGTCAATCCTG-142 | CCCATTCTTTTTCATTGTGGC-204 | 17 | 33 |
| GAPDH | NM_001034034 | GCATCGTGGAGGGACTTATGA-572 | GGGCCATCCACAGTCTTCTG-638 | 18 | 34 |
| IFNβ | M15477 | CTACAGCTTGCTTCGATTCCAA-278 | CTGCCCCAGGAGTTTCTGAC-341 | 19 | 35 |
| IL10rβ | NM_001076975 | TTTGACAAACTGAGCGTCATCA-913 | CGGCCCCAGGGTTCA-973 | 20 | 36 |
| IL28ra | XM_868941 | CCAGCTGCCGCATTGTCT-435 | TCCTTCCAGAAATTCACCTCATAGT-494 | 21 | 37 |
| IL28B | Not Assigned | ACTCATCCCTGGGCCACA-335 | GCTTGGAGTGGATGTTCTGCA-397 | 22 | 38 |
| IRF7 | BC151518 | GGACTGTGACACGCCCATCT-1535 | CCCGGAACTCCAGCAGTTC-1596 | 23 | 39 |
| ISG15 | BC102318 | GCGTGTACAAGCGGACCAGT-409 | AGCGGGTGCTCATCATCC-474 | 24 | 40 |
| MDA5 | XM_615590 | AGGAGTCAAAGCCCACCATCT-2541 | TTCTGTGTCATGGGCTTGAACT-2606 | 25 | 41 |
| MX1 | AY251193S10 | CGTCCGGAGCACGAAGAA-595 | CGTCCGGAGCACGAAGAA-650 | 26 | 42 |
| OAS1 | AY243505 | CCAAAGTTGTGAAGGGTGGC-161 | TGATCGTCCCCTGAGGGTC-216 | 27 | 43 |
| PKR | BC126646 | TGCCAAACTGGCTTATGAAAAG-545 | TCACCACACGCAGCACTGA-613 | 28 | 44 |
| RIGI 5' | XM_580928 | ACACGTCACATTTGCGGAAA-203 | CATCCGTGCATCCTCATTGA-261 | 29 | 45 |

TABLE 2

Bovine oligonucleotide probe sequences for real-time RT-PCR.

| Gene | Taq Man Probe | SEQ ID NO |
|---|---|---|
| CCL2 | CCGAGGTGCTCGCTCAGCCAG-56 | 46 |
| CCL3 | ATTTGGCGCTGACACC-144 | 47 |
| CCL20 | AGCAGCTGGCCAATGAAGCCTGTG-190 | 48 |
| CXCL10 | CCACGTGTCGAGATTA-166 | 49 |
| GAPDH | CACTGTCCACGCCATCACTGCCA-594 | 50 |
| IFNβ | ACGTCAGAGCCTTAAA-302 | 51 |
| ID10rβ | AAGTGTCTGAAAGCTGCAA-938 | 52 |
| IL28ra | CCCCAACCAGATATG-454 | 53 |
| IL28B | CCTGGAGCAGCCCCTTCTCACG-354 | 54 |
| IRF7 | ACTTCGGCACCTTCT-1558 | 55 |
| ISG15 | CTGGCTGTCTTTTGAAGGGAGGCCC-430 | 56 |
| MDA5 | ATTGGCGCTGGACACA-2563 | 57 |
| MX1 | CGTCCGGAGCACGAAGAA-614 | 58 |
| OAS1 | CTCAGGCAAAGGC-183 | 59 |
| PKR | CAGAACAATGAGAGATGG-574 | 60 |
| RIGI 5' | ACAATGATGCCCTCATT-224 | 61 |

Example 5

Bioactivity of Ad5-boIFN-λ3 in Cattle

Animal experiments were performed under the approval of the Institutional Animal Care and Use Committee (IACUC) of the Plum Island Animal Disease Center. One pilot experiment with no FMDV challenge was performed with 4 animals, each treated with $2 \times 10^{11}$ pfu of Ad5 vectors and two efficacy experiments were carried out with 14 and 12 animals respectively. All animals weighed about 400 lbs each and were kept under strict controlled conditions in the PIADC biosafety level 3 animal facilities. Efficacy studies included two independent experiments: in the first one, 14 cows were distributed in 5 groups, 4 groups (I to IV) with 3 animals each and one group (V) with 2 animals (Table 4). In the second study, 12 cows were distributed in 4 groups (I to IV) with 3 animals each (Table 6).

FMDV titers in sera and in nasal swabs were determined by standard plaque assay in BHK-21 cultured cells (Hierholzer and Killington. 1996. In: *Virology Methods Manual*, B. W. Mahy and H. O. Kangro, Editors, Academic Press Inc, San Diego, Calif., pp. 25-46). Briefly, 10-fold serial dilutions of sample were incubated for 1 h in a monolayer of BHK-21 cells. Cells were then overlaid with gum tragacanth and Eagle's minimal essential medium (MEM) containing 1% non-essential amino-acids and antibiotics, for 24 h. Cells were stained for 10 minutes with crystal violet and then washed. Titers were calculated by limited dilution of the sample where plaques were visualized. Results were expressed by $\log_{10}$/ml of sample.

In order to test the response of cattle to inoculation of Ad5-boIFN-λ3, a pilot experiment was performed with 4 animals that were inoculated with Ad5 vectors expressing IFNs as transgenes or empty vector control Ad5-Blue adapting a previously described protocol (Wu et al., supra). We chose a dose of $10^{11}$ pfu of Ad5-IFN/animal based on previous studies with type I IFN, where $10^{10}$ pfu/animal were required to induce any measurable antiviral activity in serum (Wu et al., supra). One animal (cow #933) was intramuscularly (IM) inoculated with $2 \times 10^{11}$ pfu of Ad5-Blue (control), one animal (cow #934) with $10^{11}$ pfu of Ad5-poIFNα and $10^{11}$ pfu of Ad5-Blue, one animal (cow #937) $10^{11}$ pfu of Ad5-poIFNα and $10^{11}$ pfu of Ad5-boIFN-λ3 (combination). Ad5-poIFN-α was evaluated at the same time because in previous studies we had observed that cattle inoculated with this Ad5 vector displayed the highest antiviral activity despite the species difference (Wu et al., supra). Twenty four hours after Ad5 inoculation, the animals were euthanized and necropsies were performed to isolate multiple tissues and analyze the expression of several genes by real time RT-PCR. Tissues of the respiratory tract, skin and lymphoid organs were selected based on previously reported studies about the pathogenesis of FMDV (Arzt et al., supra). Plasma was collected for measurement of IFN biological antiviral activity.

The animal inoculated with Ad5-Blue displayed a basal level of 25 U/ml IFN biological antiviral activity, animals receiving each IFN alone, 50 U/ml and the animal that received the combination, 160 U/ml. All these values were relatively low but sufficient to indicate that the Ad5 constructs were expressing the recombinant proteins. Levels of less than 25 U of antiviral activity in sera are considered basal as previously observed and reported in cattle and swine experiments (Moraes et al. supra); Wu et al., supra). The RNA levels of several genes including IFN and IFN-stimulated genes were determined by quantitative RT-PCR (qRT-PCR). In parallel, the levels of mRNA for type III IFN receptor subunits were also measured to evaluate the sensitivity of each analyzed tissue to this type of IFN. FIG. 5 shows that the expression of most of the analyzed genes was induced 2 or more fold in the Ad5-poIFN-α, Ad5-boIFN-λ3 or combination of Ad5-poIFN-α and Ad5-boIFN-λ3 treated animals in comparison to Ad5-Blue control animals. For analysis purpose an induction of 2 fold or more was considered as a "hit". While treatment with either Ad5-IFN (poIFN-α—pale yellow color—and boIFN-λ3—pale orange color—) had 84 and 92 hits respectively, treatment with the combination of Ad5-IFNs (orange color—solid and punctuated—) displayed 138 hits. Approximately 48% of these hits (solid orange) displayed enhanced expression (equivalent to the addition of each independent effect or higher) suggesting that combination treatment results in a stronger IFN response. The expression of IRF7 was synergistically induced by the combination treatment. Constitutive or up-regulated expression of type III IFN receptor (IL28-Rα and IL10-Rβ) was detected in all analyzed tissues indicating that these tissues could be susceptible to type III IFN. Interestingly, all analyzed genes were up-regulated in the naso- and oro-pharynx, tissues reported as the initial site of virus replication after aerosolization of FMDV (Arzt et al., supra).

Expression of the IFN-induced gene, Mx1, in tissues of bovines treated with Ad5-boIFN-λ3 was evaluated in immunohistochemistry (IHC) and qRTPCR assays. In IHC assays, frozen 4 µm-sections of multiple bovine tissues obtained after necropsy were mounted onto electrostatically charged glass slides (SuperFrost Plus, Fisher Scientific, Worcester, Mass.) and fixed for 10 min in acetone at −20° C. Thereafter, the slides were kept at −70° C. for up to 8 wk, until they were stained. For immunostaining, the slides were incubated with the primary antibody mouse monoclonal antibody (MAb) anti-human Mx1 (kindly provided by Dr. Otto Haller, University of Freiburg), which labels porcine Mx1 protein (Jung and Chae. 2006. *Vet. Pathol.* 43:161-167). The bound primary antibody was detected by the avidin-biotin-peroxidase complex technique (Vectastain ABC kit elite, Vector, Burlingame, Calif.) according to the manufacturer's instructions and developed either with 3, 3'-diaminobenzidine (Dako, Glostrup, Denmark) or Fast Red TR/Naphthol (Sigma, St. Louis, Mo.). Slides were counterstained with Harry's hematoxylin and coverslipped using routine methods. To control the specificity of antibody binding, a duplicate negative control serial section treated with non-specific primary antibody was used.

The expression of bovine Mx1 was evaluated by qRT-PCR in total RNA extracted from the same tissues analyzed by IHC at 24 hpi with Ad5-blue and/or Ad5-IFNs. GAPDH was used as internal control. Relative Mx1 mRNA levels were calculated in oropharynx and coronary band tissues of animals treated with Ad5-IFNs with respect to oropharynx and coronary band tissues of the animal treated with Ad5-Blue control.

Figure 6:
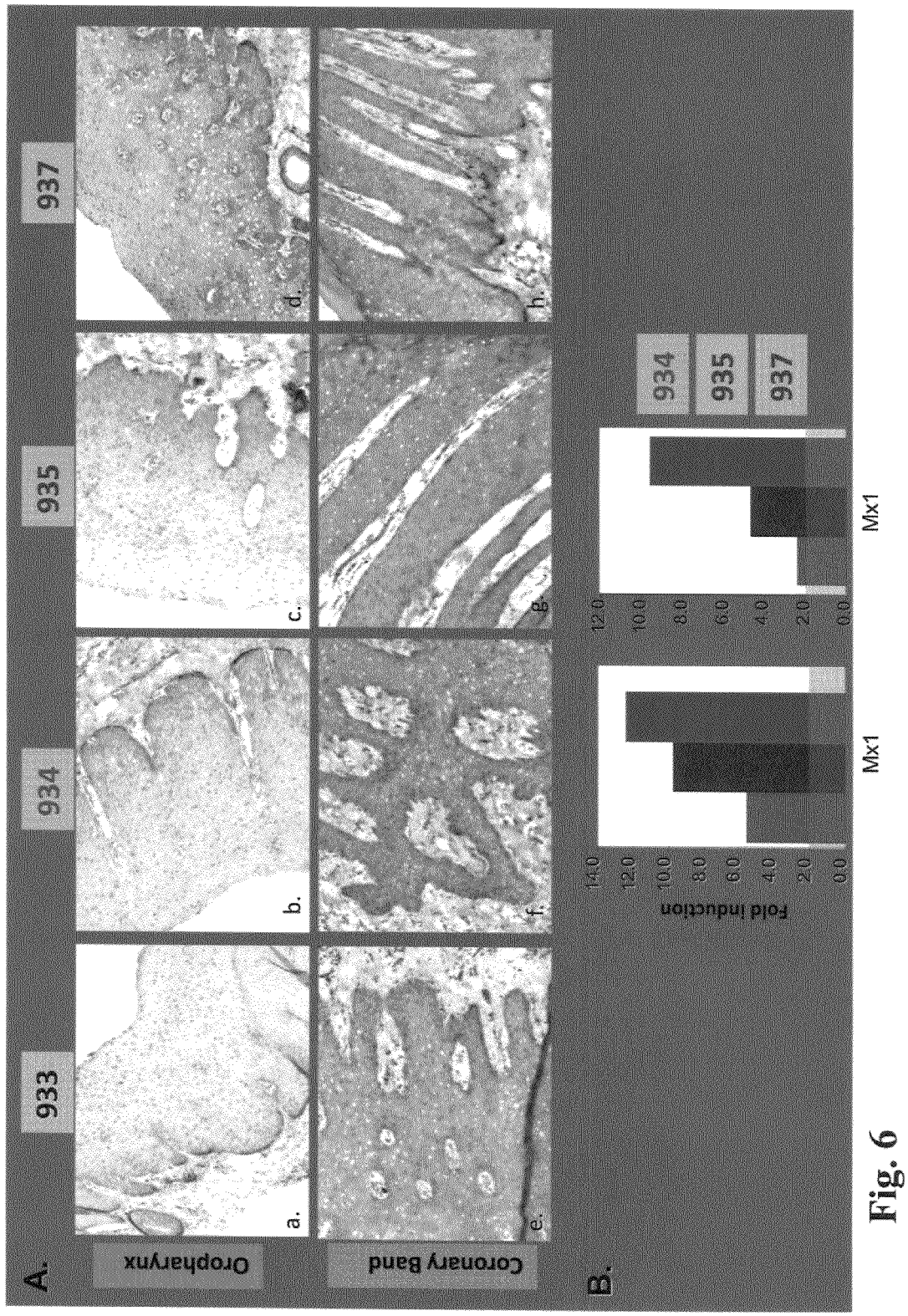
FIG. 6A depicts the results of immunohistochemistry (IHC) staining for Mx1 (an IFN-stimulated gene) after 24 h treatment with Ad5-Blue-control (cow #933), Ad5-poIFN-α (cow #934, Ad5-boIFN-λ3 (cow#935) or a combination of Ad5-boIFN-λ3 and Ad5-poIFN-α (cow#937) in bovine tissues described as the primary sites of FMDV replication. Tissue from oropharynx (panels a to d) and skin from coronary band (panels e to h) were harvested and stained with a primary antibody to detect Mx1. The bound primary antibody was detected by the avidin-biotin-peroxidase complex technique and developed with Fast Red TR/Naphthol and positivity is shown in bright purple. Sections were counterstained with Harry's hematoxylin (blue).
FIG. 6B shows the relative expression of Mx1 mRNA analyzed by qRT-PCR. Primers and probes are described in Table 1. Results are expressed as relative fold induction of tissue treated with Ad5-IFNs (cows #934, #935 and #937) with respect to tissue treated with Ad5-Blue-control (cow#933). Relative mRNA levels were determined by comparative cycle threshold analysis utilizing the samples from the Ad5-Blue-control (cow#933) as a reference. Expression of GAPDH mRNA was used as normalizer.

One day after inoculation, animals treated with Ad5-boIFN-λ3, as compared to control animals, showed increased Mx1 protein signal in the epithelium of dorsal soft palate, other mucosal epithelia and different locations of skin including coronary band or interdigital skin (FIG. 6 and Table 3). The levels of Mx1 protein detected by IHC were directly correlated with the up-regulation in the expression of mRNA analyzed by qRT-PCR. However, the signal in lymphoid tissue, palatine tonsil, retropharyngeal lymph node or spleen, was mild (Table 3). In contrast, animals inoculated with Ad5-poIFN-α showed a stronger signal in lymphoid tissues than in epithelial tissues (Table 3), and poIFN-α was also able to induce the production of Mx1 in epithelium of mucosa, dorsal soft palate, skin and other locations. The lungs were more reactive to the treatment with Ad5-poIFN-α and with Ad5-bOIFN-λ3. In all studied tissues, the signal induced by the combination of both Ad5-IFNs was higher than each individual treatment.

TABLE 3

Expression of Mx1 in different tissues in animals treated with Ad5-poIFN-α, Ad5-boIFN-λ3 or the combination of the two.

|  | Ad5-poIFN-α | Ad5-boIFN-λ3 | Combination |
|---|---|---|---|
| Dorsal Soft Palate | $+^a/2.9^b$ | ++/2.1 | +++/6.9 |
| Oropharynx | ±/5.7 | ++/9.7 | +++/12.4 |
| Nasopharynx | +/20.5 | ++/15.0 | +++/28.6 |
| Proximal Lung | ++/2.3 | ±/1.0 | +++/4.2 |
| Tongue | ±/3.1 | ++/13.4 | +++/11.2 |
| Retro LN | ++/2.3 | +/1.1 | ++/1.7 |
| Palatine Tonsil | +++/2.4 | +/1.7 | +++/4.9 |
| Spleen | ++/3.9 | ±/0.7 | ++/5.9 |
| Skin Interdigital | ±/15.9 | +/7.2 | ++/11.9 |
| Skin Coronary Band | ±/2.4 | +/4.7 | ++/9.6 |

[a] Semi-quantitative analysis of Mx1 protein signal in tissue sections detected by IHC: − is negative and +++ maximum signal (± < + < ++ < +++).
[b] Level of fold induction of mRNA detected in each tissue detected by Real Time RT- PCR, compared with the same tissue in a non-treated animal. Only animals with and expression ≥2 are considered up-regulated.

These results indicated the identified boIFN-λ3 has antiviral activity in cattle in vivo and induces the expression of several IFN-stimulated genes when used alone or in combination with IFN-α preferably targeting mucosal tissues including those primary sites of FMDV replication Example 6

Efficacy of Ad5-boIFN-λ3 Treatment Against FMDV Challenge by Direct Inoculation

Based on the results of the pilot study showing that boIFN-λ3 was biologically active in vivo, we designed another experiment to determine the efficacy of Ad5 boIFN-λ3 treatment against FMDV. Fourteen animals were inoculated with Ad5 vectors following the experimental design described in Table 4. Cattle from group I and II were intramuscularly (IM) inoculated in the neck with a combination of Ad5-boIFN-λ3 and Ad5-poIFN-α at doses of $1\times10^{11}$ pfu and $0.5\times10^{11}$ pfu of each recombinant Ad5, respectively, in a total volume of 2 ml. Groups III and IV were inoculated with $1\times10^{11}$ pfu of Ad5-pIFN-α and $1\times10^{11}$ pfu Ad5-bIFN-λ3, respectively. The remaining group (V) was inoculated with $1\times10^{11}$ pfu Ad5-Blue as a control. One day after the Ad5 inoculation, all animals were challenged by intradermolingual (IDL) inoculation with $1\times10^{4}$ BID$_{50}$ of A24 Cruzeiro FMDV. IDL inoculation was chosen as the starting point based on OIE standards and previous testing (OIE 2010 supra; Wu et al., 2003 supra). Clinical signs, viremia, virus shedding (nasal swabs) and antiviral activity were monitored up to 21 days post challenge. Rectal temperatures were measured daily during the experiment. Animals were examined in detail for the presence of FMD clinical signs and lesions, every 2 days after the FMDV challenge. A maximum clinical score was considered as 5 counting the presence of lesions in each foot (4) and in the mouth (1), in a region other than the inoculation site. Animals were bled daily from the day of vaccination (−1 dpc) until 7 dpc and at 14 and 21 dpc, for viremia, serology analysis and antiviral activity determination.

Figure 7:
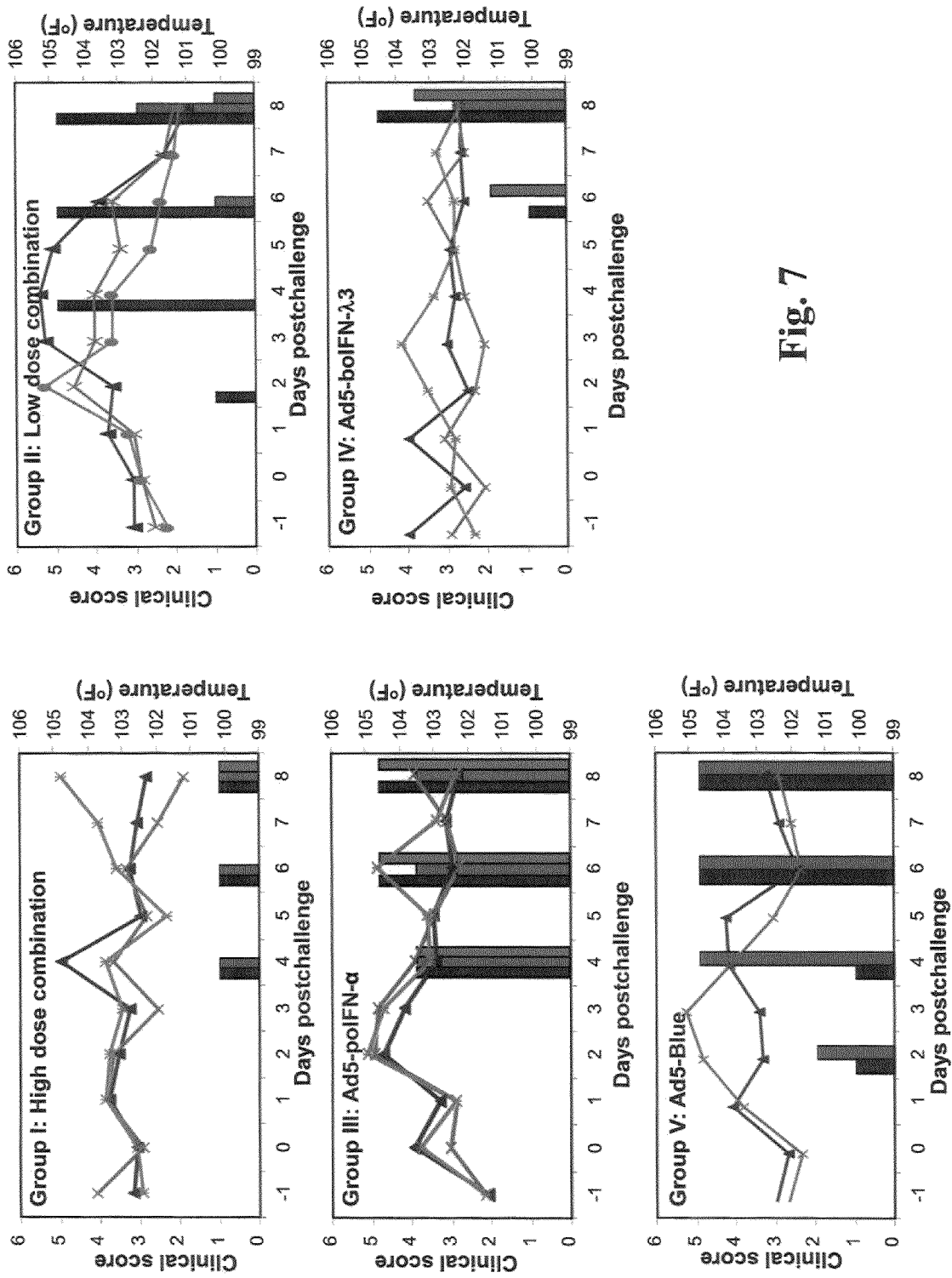
FIG. 7 depicts results of efficacy study #1 in bovines. Four groups (Gp I-IV) of 3 bovines each were treated with Ad5-IFNs and one group (Gp V) of 2 bovines was treated with Ad5-Blue-control. Gp I: High Dose Combination: Ad5-poIFN-α ($1 \times 10^{11}$ pfu)+Ad5-boIFN-λ3 ($1 \times 10^{11}$ pfu); Gp II: Low Dose Combination: Ad5-poIFN-α ($0.5 \times 10^{11}$ pfu)+Ad5-boIFN-λ3 ($0.5 \times 10^{11}$ pfu); Gp III: Ad5-poIFN-α ($1 \times 10^{11}$ pfu); Gp IV: Ad5-boIFN-λ3 ($1 \times 10^{11}$ pfu); Gp V: Ad5-Blue ($1 \times 10^{11}$ pfu). At 24 h animals were challenged with $10^4$ $BID_{50}$ of FMDV A24 Cruzeiro by intradermolingual direct inoculation. Clinical scores (bars) and temperatures in Fahrenheit scale (lines) were evaluated for 8 days post Ad5 inoculation. Each color represents one animal from each group.

The results of clinical signs and rectal temperatures are shown in FIG. 7. Different degrees of protection were observed among the groups. In the high combination group, 2/3 animals developed 1 lesion by 4 dpc and the remaining animal developed 1 lesion by 6 dpc, however the clinical score did not increase thereafter and FMD was resolved normally. In the low combination group one animal developed lesions by 2 dpc, with a score of 1 that increased to 5 by 4 dpc, but the other two animals remained disease free until day 8. All animals inoculated with Ad5-poIFN-α alone (3/3) displayed lesions by 4 dpc with an average clinical score of 4. Interestingly, only one animal in the group inoculated with Ad5-boIFN-λ3, developed lesions by 6 dpc, although all animals were sick by 8 dpc. Animals inoculated with control Ad5-Blue (2/2) developed clinical signs by 2 dpc. In general, high rectal temperatures (>104° F.) preceded appearance of clinical signs and consistently, the groups treated with Ad5-boIFN-λ3 or high dose IFN combination, that displayed reduced severity of FMD, did not develop fever. In most of the animals, viremia was detected between 1 to 3 dpc and virus nasal shedding between 1 to 4 dpc, despite the delay in the appearance or reduced severity of clinical signs for the groups treated with Ad5-boIFN-λ3 or Ad5-IFN combinations (Table 5). Variable levels of antiviral activity were detected in the plasma of all animals. We could not detect a direct correlation between the levels of antiviral activity and protection. Although low levels (25-50 U) of systemic antiviral activity were detected in the animals treated with Ad5-boIFN-λ3, disease was delayed until 6 dpc. In the high combination group, higher levels (100-200 U) of antiviral activity were detected and although animals developed 1 lesion by 4 dpc, disease did not progress further. In contrast, all animals of the group treated with Ad5-poIFN-α which had similar levels of antiviral activity (100-200 U) developed disease by 4 dpc with the highest scores (5).

Overall, these results suggested that treatment of cattle with Ad5 boIFN-λ3 alone or in combination with IFN-α caused delayed and reduced severity of disease after intradermolingual challenge with FMDV.

TABLE 4

Efficacy Study N°1 in Cattle.

| Group | Treatment (Ad5-dose) | # of Animals | FMDV Challenge |
| --- | --- | --- | --- |
| I | Ad5-poIFN-α + Ad5-boIFN-λ3 ($1 \times 10^{11}$ pfu) ($1 \times 10^{11}$ pfu) | 3 | $1 \times 10^{4}$ BID$_{50}$ A24 Cruzeiro |
| II | Ad5-poIFN-α + Ad5-boIFN-λ3 ($0.5 \times 10^{11}$ pfu) ($0.5 \times 10^{11}$ pfu) | 3 | $1 \times 10^{4}$ BID$_{50}$ A24 Cruzeiro |
| III | Ad5-poIFN-α ($1 \times 10^{11}$ pfu) | 3 | $1 \times 10^{4}$ BID$_{50}$ A24 Cruzeiro |
| IV | Ad5-boIFN-λ3 ($1 \times 10^{11}$ pfu) | 3 | $1 \times 10^{4}$ BID$_{50}$ A24 Cruzeiro |
| V | Ad5-Blue ($1 \times 10^{11}$ pfu) | 2 | $1 \times 10^{4}$ BID$_{50}$ A24 Cruzeiro |

TABLE 5

Summary of Efficacy Study with direct inoculation challenge

| Groups | Cow ID# | Clinical Signs[a] Day of onset/CS | Viremia[b] | Nasal Shedding[c] ($\log_{10}$) | Antiviral Activity[d] |
| --- | --- | --- | --- | --- | --- |
| High Dose Combination | 9171 | 4/1 | 3/2/2.90 | 3/2/4.75 | 200 |
| Ad5-poIFN-α + Ad5-boIFN-λ3 | 9172 | 4/1 | 3/2/3.15 | 3/2/3.66 | 100 |
| (each $1 \times 10^{11}$ pfu) | 9173 | 8/1 | 3/2/2.89 | 3/2/2.51 | 200 |
| Low Dose Combination | 9174 | 1/5 | 2/3/4.36 | 2/3/3.97 | <25 |
| Ad5-poIFN-α + Ad5-boIFN-λ3 | 9175 | 6/3 | 2/3/3.40 | 3/2/2.92 | 100 |
| (each $0.5 \times 10^{11}$ pfu) | 9176 | 8/1 | 2/3/2.7 | 2/3/4.24 | 25 |
| Ad5-poIFN-α | 9177 | 4/5 | 2/3/3.64 | 0.00 | 200 |
| ($1 \times 10^{11}$ pfu) | 9178 | 4/4 | 1/3/4.04 | 2/3/3.47 | 400 |
| | 9179 | 4/5 | 2/2/3.14 | 2/3/6.54 | 50 |
| Ad5-boIFN-λ3 | 9180 | 6/5 | 3/2/2.81 | 0.00 | 50 |
| ($1 \times 10^{11}$ pfu) | 9181 | 8/5 | 3/3/3.04 | 4/1/2.86 | 50 |
| | 9182 | 6/3 | 2/3/3.44 | 3/2/3.14 | 25 |
| Ad5-Blue | 9183 | 2/5 | 3/1/2.63 | 2/3/3.51 | 50 |
| ($2 \times 10^{11}$ pfu) | 9184 | 2/5 | 1/3/4.15 | 1/4/4.91 | <25 |

[a]Day of onset of FMD clinical signs after challenge/maximum clinical score reached until day 8 dpc.
[b]Day of the onset of viremia after challenge/duration in days/peak titer of viremia reached along the experiment, expressed as $\log_{10}$ pfu/ml.
[c]Day of the onset of nasal shedding after the challenge/duration in days/peak of viral shedding reached along the experiment, expressed as $\log_{10}$ pfu/ml.
[d]Antiviral activity in units/ml from plasma at 0 dpc.

Example 7

Efficacy of Ad5-boIFN-λ3 Treatment Against FMDV Challenge by Aerosol Exposure Another experiment to determine the efficacy of Ad5 boIFN-λ3 treatment against FMDV was performed but viral challenge was performed by aerosol exposure to FMDV serotype O1 Manisa. Twelve animals were inoculated with Ad5 vectors or PBS following the experimental design described in Table 6. Cattle from group I were subcutaneously (SC) inoculated in two sites of the neck with a combination of Ad5-boIFN-λ3 and Ad5-boIFN-α at a dose of $7 \times 10^{10}$ pfu of each recombinant Ad5 in a total volume of 6 ml. Groups II and III were inoculated with $1.5 \times 10^{11}$ pfu of Ad5-boIFN-α and $1.5 \times 10^{11}$ pfu Ad5-boIFN-λ3, respectively. The remaining group (IV) was inoculated with PBS as a control. One day after the Ad5 inoculation, all animals were challenged by aerosol exposure with $1 \times 10^7$ pfu of O1 Manisa FMDV, using a method that resembles natural infection (Pacheco, Arzt et al supra). In brief, cattle was sedated with xylazine (0.1-0.3 mg/kg) IM prior to virus exposure which was reversed with tolazine (2-4 mg/kg slow IV) after exposure. Animals were monitored (heart rate, respiratory rate) until recovery (standing). FMDV O1 Manisa ($10^7$ pfu in 2 ml of PBS) were nebulized using a compressed air tank and a commercially aerosol delivery system comprised of a jet nebulizer (Whisper Jet, Marquest Medical Products, CO), holding chamber and mask (Equine Aeromask, Trudell Medical, London, ON, Canada). Compressed air (25 psi) was used to jet-nebulize the inoculum directly into the holding chamber. Upon inspiration, the nebulized inoculum was inhaled through a one-way valve into the mask and directly into the nostrils. Clinical signs, viremia, virus shedding (nasal swabs) and antiviral activity were monitored up to 21 days post challenge. Rectal temperatures were measured daily during the experiment. Animals were examined in detail for the presence of FMD clinical signs and lesions, every 2 days after the FMDV challenge. A maximum clinical score was considered as 5 counting the presence of lesions in each foot (4) and in the mouth (1), in a region other than the inoculation site. Animals were bled daily from the day of vaccination (−1 dpc) until 7 dpc and at 14 and 21 dpc, for viremia, serology analysis and antiviral activity determination.

TABLE 6

Efficacy Study N°2 in Cattle.

| Group | Treatment (Ad5-dose) | # of Animals | FMDV Challenge |
|---|---|---|---|
| I | Ad5-boIFN-α + Ad5-boIFN-λ3 (each $7.5 \times 10^{10}$ pfu) | 3 | $1 \times 10^7$ pfu O1 Manisa |
| II | Ad5-boIFN-α ($1.5 \times 10^{11}$ pfu) | 3 | $1 \times 10^7$ pfu O1 Manisa |
| III | Ad5-boIFN-λ3 ($1.5 \times 10^{11}$ pfu) | 3 | $1 \times 10^7$ pfu O1 Manisa |
| IV | PBS | 3 | $1 \times 10^7$ pfu O1 Manisa |

Figure 8:
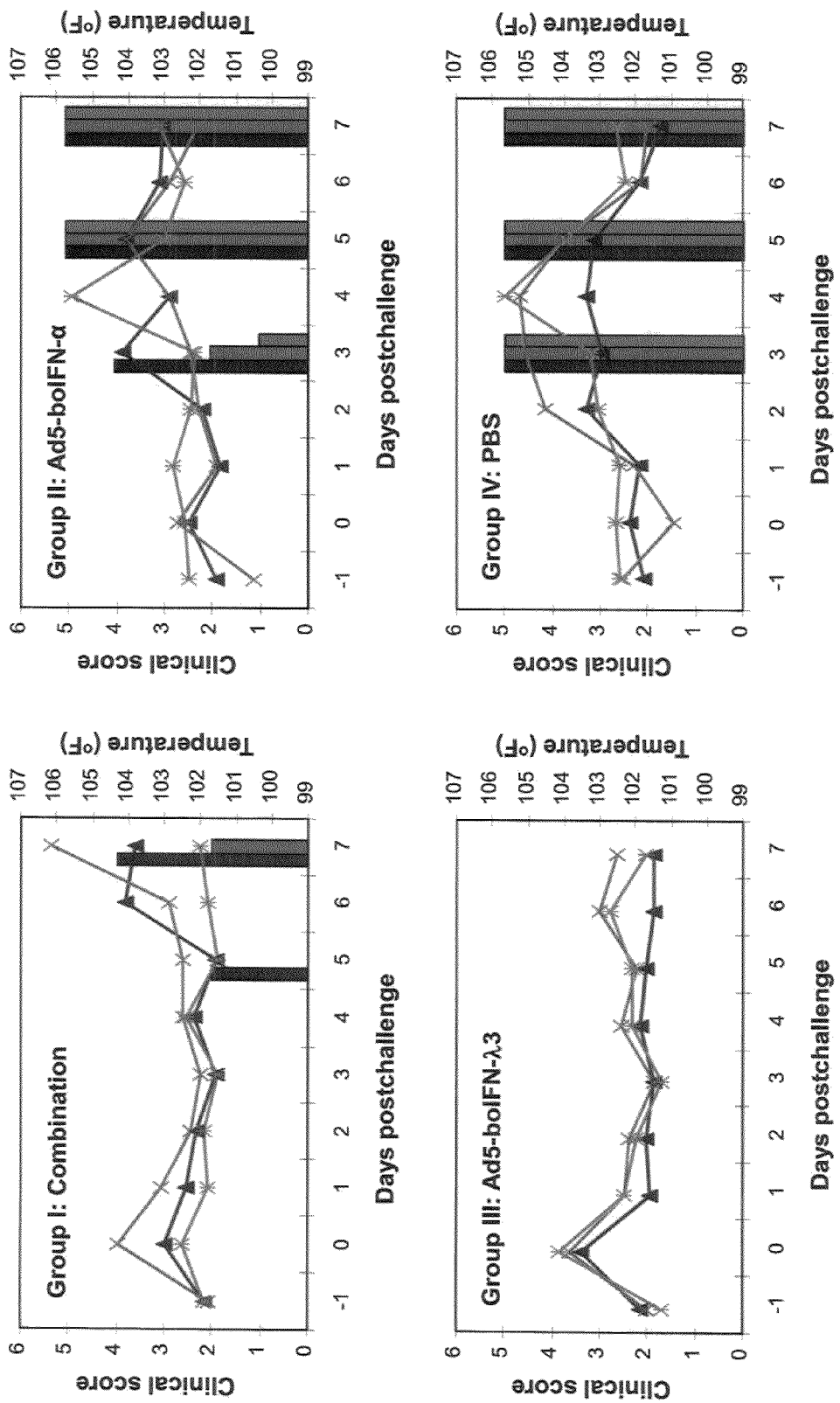
FIG. 8 depicts results of an efficacy study #2 in bovines. Three groups (Gp I-III) of 3 bovines each were treated with Ad5-IFNs and one group (Gp IV) of 3 bovines was treated with PBS control. Gp I: Combination: Ad5-boIFN-α ($7.5 \times 10^{10}$ pfu)+Ad5-boIFN-λ3 ($7.5 \times 10^{10}$ pfu); Gp II: Ad5-boIFN-α ($1.5 \times 10^{11}$ pfu); Gp III: Ad5-boIFN-λ3 ($1.5 \times 10^{11}$ pfu); Gp IV: PBS. At 24 h animals were challenged with $10^7$ pfu of FMDV O1Manisa by aerosol exposure. Clinical scores (bars) and temperatures in Fahrenheit scale (lines) were evaluated for 7 days post Ad5 inoculation. Each color represents one animal from each group.

The results of clinical signs and rectal temperatures are shown in FIG. 8. Control animals developed clinical signs of disease by 3 dpc with the highest score of 5. Animals treated with $1.5 \times 10^{11}$ pfu/animal of Ad5-boIFN-α also showed clinical signs starting at 3 dpc, but with less severity than control animals: one animal had a score of 1, one had a score of 2 and the other had a score of 4. Animals inoculated with the combination of Ad5-boIFN-α and Ad5-boIFN-λ3 ($7.5 \times 10^{10}$ pfu/animal each) showed a clear delay on the onset of disease, 5-7 days with low scores of 1-4, and one animal of this group did not show clinical signs of disease even by 7 dpc. Remarkably, animals that received Ad5-boIFN-λ3 at a dose of $1.5 \times 10^{11}$ pfu/animal did not show signs of disease for 7 days post FMDV exposure. By 9 days only 1 animal had a lesion, a clear sign of reduced severity of disease. By day 12 post FMDV exposure one animal still remained disease free, while the other two had low scores, 1 and 3 respectively. These results indicated that administration of Ad5-boIFN-λ3 can protect cattle from challenge with FMDV by a method resembling the natural route of infection.

Example 8

Bioactivity of Bovine IFN-α

The level of in vivo expression of boIFN-α was examined in three bovines. Three Holstein cattle (6-8 months old, 450-500 lbs each) were inoculated intramuscularly in the neck with $1 \times 10^9$, $2.5 \times 10^9$, $5 \times 10^9$ pfu/animal of Ad5-boIFN-α, respectively. One bovine was inoculated with $5 \times 10^9$ pfu Ad5-VSVG (VSV G viral protein) as a control. Animals were monitored for adverse clinical effects of IFN administration, and temperature was taken daily. Plasma was taken before inoculation and daily until 7 dpi and assayed for antiviral activity in MDBK cells. None of the animals displayed abnormal behavior or had elevated temperatures. No antiviral response was detectable in any of the inoculated animals (data not shown). However, all animals developed a significant Ad5-specific neutralizing antibody response at 13 dpi, indicating that they were exposed to the recombinant virus.

Given that no antiviral activity was detected in the sera of the cows used in our initial experiment with Ad5 boIFN-α, we tested the ability of the same Ad5-boIFN-α to express biologically active boIFN-α in vivo but in a different species e.g. swine. We had previously shown that boIFN-α induces antiviral activity in swine cultured cells (Wu et al supra). Swine were inoculated with different doses of Ad5-boIFN-α followed by monitoring systemic antiviral in plasma samples. By 1 dpi, the swine inoculated with $1 \times 10^9$ pfu Ad5-boIFNα developed an antiviral response of 50 U/ml. The animal inoculated with $5 \times 10^9$ pfu had higher activity (100 U/ml) by 1 dpi, but in each case, the antiviral activity was detectable for only one day.

These data demonstrated that Ad5-boIFN-α can express biologically active boIFN-α in animals.

The efficacy of Ad5-boIFN-α alone or in combination with type II IFN (boIFN-γ) was tested in bovines (Table 7). Twelve cows (400-500 lb) were divided in 4 groups of 3 animals each. Each group was intramuscularly inoculated with $2 \times 10^{10}$ pfu of Ad5-Blue, $1 \times 10^{10}$ pfu of Ad5-boIFN-α plus $1 \times 10^{10}$ pfu of Ad5-Blue, $1 \times 10^{10}$ pfu of Ad5-boIFN-γ plus $1 \times 10^{10}$ pfu of Ad5-Blue, or $1 \times 10^{10}$ pfu of Ad5-boIFN-α plus $1 \times 10^{10}$ pfu of Ad5-boIFN-γ. Twenty four hours post inoculation the animals were challenged with $10^4$ BID$_{50}$ of A24-FMDV. Viremia and clinical signs were monitored for 7 days.

A10 animals inoculated with Ad5-Blue developed disease by 2 days after challenge with scores reaching the maximum of 5. The group inoculated with Ad5-boIFN-γ plus Ad5-Blue developed clinical signs of disease between 2 to 7 days post challenge and the clinical score varied from 1 to 3. One animal of the group inoculated with Ad5-boIFN-α plus Ad5-Blue was protected from disease and the other two developed lesions with scores of 1 and 3 by 5 and 3 days post inoculation. Interestingly, in the group inoculated with the combination of Ad5-boIFN-α plus Ad5-boIFN-γ, two animals were protected from disease and the remainder had a clinical score of 3 by 6 days post challenge. All animals developed viremia between 1 and 2 days post challenge.

These results indicated that inoculation of cattle with Ad5-boIFN-α alone or in combination with Ad5-boIFN-γ results in delayed and reduced severity of FMD.

TABLE 7

Dose response of Ad5-boIFN-α and Ad5-boIFN-γ in cattle.

| GROUPS | Cow# | CLINICAL SIGNS[a] Day of Onset/Score | VIREMIA[b] First dpc/dur/peak |
|---|---|---|---|
| Ad5-boIFN-α + Ad5-boIFN-γ Combination ($1 \times 10^{10}$ pfu + $1 \times 10^{10}$ pfu) | 166 | 0/0 | 1/4/3.13 |
| | 176 | 6/3 | 1/4/3.20 |
| | 180 | 0/0 | 1/2/1.27 |
| Ad5-boIFN-α + Ad5-Blue ($1 \times 10^{10}$ pfu + $1 \times 10^{10}$ pfu) | 750 | 0/0 | 2/3/2.84 |
| | 752 | 5/1 | 2/3/3.17 |
| | 753 | 3/3 | 2/3/3.22 |
| Ad5-boIFN-γ + Ad5-Blue ($1 \times 10^{10}$ pfu + $1 \times 10^{10}$ pfu) | 754 | 7/1 | 1/3/2.08 |
| | 758 | 2/3 | 1/3/3.38 |
| | 761 | 5/2 | 1/3/2.88 |
| Ad5 Blue ($2 \times 10^{10}$ pfu) | 764 | 2/5 | 1/3/3.13 |
| | 765 | 2/5 | 1/3/3.39 |
| | 778 | 2/5 | 1/3/3.42 |

[a]Day of onset of FMD clinical signs after challenge/maximum clinical score reached until day 7 dpc. Maximum clinical score is 5.
[b]Day of the onset of viremia after challenge/duration in days/peak titer of viremia reached along the experiment, expressed as $\log_{10}$ pfu/ml.

Example 9

Bioactivity of Porcine Type I IFN (α/β)

Ad5-mediated expression of poIFN-α and poIFN-β was evaluated in cattle and swine. In a dose-response experiment, cattle (450-500 lbs) and swine (35-40 lbs) were inoculated IM with $1 \times 10^9$ or $5 \times 10^9$ pfu Ad5-poIFN-α or Ad5-poIFN-β. Plasma was taken before inoculation and daily until 7 dpi and assayed for antiviral activity in IBRS2 cells. The level of poIFN-α expression in Ad5-poIFN-β-inoculated animals was determined by ELISA. All the inoculated cattle behaved normally and did not develop fever. Only the bovine inoculated with the high dose ($5 \times 10^9$ pfu) of Ad5-poIFN-α developed an antiviral response (50 U/ml) and had a very low level of poIFN-α (63 pg/ml) protein in plasma, each detectable for only 1 day (Table 8). In contrast, swine inoculated with either $1 \times 10^9$ or $5 \times 10^9$ pfu of Ad5-poIFN-α developed an antiviral response (400 and 800 U/ml, respectively) by 1 dpi, which lasted for an additional 3-4 days.

TABLE 8

Dose response of Ad5-poIFN-α and Ad5-poIFN-β in cattle and swine.

| Inoculum | Dose | Species | Antiviral Activity[a] | | | | | |
|---|---|---|---|---|---|---|---|---|
| | | | 0 dpi | 1 dpi | 2 dpi | 3 dpi | 4 dpi | 5 dpi |
| Ad5-VSVG | $5 \times 10^9$ | swine | <25 | <25 | <25 | <25 | <25 | <25 |
| | | bovine | <25 | <25 | <25 | <25 | <25 | <25 |
| Ad5-poIFNα | $1 \times 10^9$ | swine | <25 | 400 | 200 | 100 | <25 | <25 |
| | | bovine | <25 | <25 | <25 | <25 | <25 | <25 |
| | $5 \times 10^9$ | swine | <25 | 800 | 800 | 400 | 100 | <25 |
| | | bovine | <25 | 50 | <25 | <25 | <25 | <25 |
| Ad5-poIFNβ | $1 \times 10^9$ | swine | <25 | <25 | <25 | <25 | <25 | <25 |
| | | bovine | <25 | <25 | <25 | <25 | <25 | <25 |
| | $5 \times 10^9$ | swine | <25 | <25 | <25 | <25 | <25 | <25 |
| | | bovine | <25 | <25 | <25 | <25 | <25 | <25 |

[a]Highest dilution that reduced FMDV A12 plaque number by 50% in IBRS2 cells

Our results indicate that poIFN-α is active in cattle and swine, supporting its use as a biotherapeutics in both species.

Example 10

Immunopotentiation of a FMDV Subunit Vaccine by Porcine Interferon-α

The adjuvant effect of porcine interferon alpha (poIFN-α) was examined in swine vaccinated with Ad5 FMD vaccine expressing A24 capsid and 3C proteinase coding regions (Ad5-A24). Groups of swine were inoculated with either high ($5\times10^9$ pfu) or low ($5\times10^8$ pfu) doses of Ad5-A24 in the presence or absence of Ad5-poIFN-α ($1\times10^9$ pfu) or with a control Ad5-VSNJV-G followed by challenge by intradermal inoculation in the heel bulb with $10^4$ $PIG_{50}$ A24 of FMDV at 42 days post-vaccination. After challenge all control animals developed viremia and lesions.

Animals receiving low-dose Ad5-A24 had similar clinical disease, but only three of five animals developed viremia. Interestingly, addition of IFN resulted in a delayed onset of lesions in three animals and only one animal had detectable viremia. Animals vaccinated with high-dose Ad5-A24 had no viremia, significantly fewer lesions and delayed onset of disease compared to the control and low-dose vaccine groups. Four of five pigs vaccinated with high-dose Ad5-A24 plus IFN were completely protected from disease and only one animal had a lesion which was restricted to the site of challenge (Table 9).

Our results indicate that poIFN-α enhances the long-term level of protection induced by the Ad5-FMD vaccine, supporting its use as a potential adjuvant in FMD vaccination strategies.

TABLE 9

Adjuvant effect of poIFNα when used in combination with FMD vaccine.

| | | | Peak Viral Titer | | NS | | |
|---|---|---|---|---|---|---|---|
| Group | # | Clinical Score[a] | Blood | Nasal Fluid | Protein 3ABC[b] | RIP[c] | PRN70[g] |
| High Ad5-A24 | 3855 | 0 | 0 | 0 | – | – | 512 |
| Ad5-pIFN-α | 3856 | 0 | 0 | 0 | – | – | 256 |
| | 3857 | 0 | 0 | 0 | – | – | 128 |
| | 3858 | 0 | 0 | 0 | + | – | 64 |
| | 3859 | 1[d] (3[e]) | 0 | 0 | ++ | – | 256 |
| Low Ad5-A24 | 3860 | 5 (5) | 0 | 20 (3[f]) | ++ | ++ | 16 |
| Ad5-pIFN-α | 3861 | 16 (2) | 250 (4[f]) | 2000 (5) | +++ | ++ | 16 |
| | 3862 | 3 (7) | 0 | 100 (3) | +/– | – | 16 |
| | 3863 | 14 (3) | 0 | 350 (3) | +++ | +/– | 32 |
| | 3864 | 13 (5) | 0 | 225 (3) | +++ | ++ | 32 |

TABLE 9-continued

Adjuvant effect of poIFNα when used in combination with FMD vaccine.

| Group | # | Clinical Score[a] | Peak Viral Titer | | NS Protein 3ABC[b] | RIP[c] | PRN70[g] |
|---|---|---|---|---|---|---|---|
| | | | Blood | Nasal Fluid | | | |
| High Ad5-A24 Ad5-Blue | 3865 | 1[d] (10) | 0 | 30 (5) | − | +/− | 256 |
| | 3866 | 1 (4) | 0 | 35 (4) | + | + | 256 |
| | 3867 | 2[d] (5) | 0 | 10 (5) | + | + | 64 |
| | 3868 | 0 | 0 | 0 | − | + | 256 |
| | 3869 | 2[d] (6) | 0 | 50 (2) | ++ | − | 128 |
| Low Ad5-A24 Ad5-Blue | 3870 | 13 (3) | 0 | 1000 (3) | +++ | + | 8 |
| | 3871 | 17 (2) | 725 (3) | 6000 (4) | ++ | + | 8 |
| | 3872 | 16(2) | 72500 (3) | 550 (4) | ++ | +++ | 8 |
| | 3873 | 17(3) | 9500 (4) | 500 (2) | +++ | ++ | 8 |
| | 3874 | 8 (2) | 0 | 500 (3) | ++ | + | 32 |
| Ad5-VSNJV-G | 3875 | 15 (3) | 22250 (3) | 350 (3) | +++ | +++ | <8 |
| | 3876 | 16 (2) | 67500 (3) | 14000 (3) | +++ | +++ | <8 |
| | 3877 | 16 (2) | 157500 (3) | 600 (3) | ++ | +++ | <8 |
| | 3878 | 17 (2) | 4750 (3) | 65 (4) | +++ | ++ | <8 |
| | 3879 | 16 (2) | 16500 (3) | 1450 (3) | +++ | +++ | <8 |

Animal Number
[a]The clinical score was determined by the number of toes with lesions and the presence of lesions on the snout or tongue. The maximum score is 17.
[b]Data from serum collected at 63 dpc; (−) negative, (+/−) suspicious, (+) weak positive, (++) positive, and (+++) high positive.
[c]Radioimmunoprecipitation.
[d]Lesion at site of inoculation.
[e]Date in parenthesis indicates the dpc when the vesicular lesions were first observed.
[f]Date in parenthesis indicates the dpc with highest viral titer and are expressed in plaque-forming units (PFU/ml).
[g]Neutralizing antibody response reported as serum dilution yielding a 70% reduction in the number of plaques (PRN70) at the day of challenge (42 dpv).

All publications and patents mentioned in this specification are herein incorporated by reference to the same extent as if each individual publication or patent was specifically and individually indicated to be incorporated by reference.

The foregoing description and certain representative embodiments and details of the invention have been presented for purposes of illustration and description of the invention. It is not intended to be exhaustive or to limit the invention to the precise forms disclosed. It will be apparent to practitioners skilled in this art that modifications and variations may be made therein without departing from the scope of the invention.

We claim:

1. An isolated or recombinant cDNA comprising a sequence that encodes bovine interferon-λ3 (boIFN-λ3).

2. An isolated or recombinant cDNA comprising a sequence that encodes a polypeptide having the amino acid sequence set forth in SEQ ID NO:2.

3. An isolated or recombinant cDNA comprising the sequence set forth in SEQ ID NO:1.

4. An effective antiviral pharmaceutical composition comprising an effective amount of an isolated or recombinant bovine IFN-λ3 (boIFN-λ3) cDNA wherein the composition is capable of inducing systemic antiviral anti-foot and mouth disease virus (FMDV) activity.

5. An effective antiviral pharmaceutical composition comprising an effective amount of an isolated or recombinant bovine IFN-λ3 (boIFN-λ3) cDNA and an isolated or recombinant porcine or bovine type I IFN cDNA wherein the composition is capable of inducing systemic antiviral anti-foot and mouth disease virus (FMDV) activity.

6. An effective antiviral pharmaceutical composition comprising a vector containing an isolated or recombinant cDNA encoding bovine interferon-λ3 (boIFN-λ3).

7. An effective antiviral pharmaceutical composition comprising a combination of a vector containing an isolated or recombinant cDNA encoding bovine interferon-λ3 (boIFN λ3) and a vector containing an isolated or recombinant cDNA encoding porcine or bovine type I interferon or FMD vaccine wherein the compositions are capable of inducing systemic antiviral anti-foot and mouth disease virus (FMDV) activity and of inducing up-regulation of interferon-stimulated gene expression in vivo, and thereby acting to delay and reduce severity of foot and mouth disease (FMD).

8. The effective antiviral pharmaceutical composition of any one of claims 4-7 further comprising an adjuvant.

9. A method of reducing the degree or rate of infection by foot and mouth disease virus (FMDV) in an animal comprising:
administering to said animal an effective dosage of the antiviral pharmaceutical composition of claim 5 comprising a combination of a vector containing an isolated or recombinant cDNA encoding bovine interferon-λ3 (boIFN-λ3) and a vector containing an isolated or recombinant cDNA encoding porcine or bovine Type I interferon wherein the compositions are capable of inducing systemic antiviral anti-foot and mouth disease virus (anti-FMDV) activity and of inducing up-regulation of interferon-stimulated gene expression in vivo, and said animal has delayed and reduced severity of foot and mouth disease as compared to an infected animal not treated with said pharmaceutical composition.

10. A method of reducing the degree or rate of infection by FMDV in an animal comprising:
administering to said animals an effective dosage of an antiviral pharmaceutical composition comprising a combination of the vector containing an isolated or recombinant cDNA encoding bovine interferon-λ3 (boIFN-λ3) of claim 6 and a vector containing an isolated or recombinant cDNA encoding the capsid of FMDV, wherein the composition is capable of inducing systemic antiviral anti-foot and mouth disease virus (FMDV) activity and of inducing the production of neutralizing antibodies in vivo, and said animal has delayed and reduced severity of foot and mouth disease as compared to an infected animal not treated with said pharmaceutical composition.

11. A method of inducing expression of IFN-stimulated genes correlated with systemic control of viral replication in an animal susceptible to FMDV comprising:
   administering to said animal an effective dosage of the antiviral pharmaceutical composition of claim 5 comprising a combination of a vector containing an isolated or recombinant cDNA encoding bovine interferon-λ3 (boIFN-λ3) and a vector containing isolated or recombinant cDNA encoding porcine or bovine type I interferon wherein up-regulation of specific gene expression of IFN-stimulated genes correlated with systemic control of FMDV replication in vivo, is induced in said animal.

12. A method of inducing expression of Type III IFN receptors in tissues of the upper airways of an animal susceptible to FMDV comprising:
   administering to said animal an effective dosage of the antiviral pharmaceutical composition of claim 5 comprising a combination of a vector containing an isolated or recombinant cDNA encoding bovine interferon-λ3 (boIFN-λ3) and a vector containing an isolated or recombinant cDNA encoding porcine or bovine type I interferon wherein expression of Type III IFN receptors in tissues of the upper airways of said animal is induced.

13. The method of any one of claims 9-12 wherein said animals susceptible to FMD are swine, cattle, goats, or sheep.

* * * * *

```
                        SEQUENCE LISTING

<160> NUMBER OF SEQ ID NOS: 61

<210> SEQ ID NO 1
<211> LENGTH: 588
<212> TYPE: DNA
<213> ORGANISM: Bos taurus

<400> SEQUENCE: 1
atggccccgg gctgcacgct ggtgctggtg ctgatgctga cgaccgtggc gctgagcagg      60
acaggagcag ttcctgtgcc ctctgccccc agggccctcc cacctgccag gggctgccac     120
gtggcccagt tcaagtctct gtcccctcaa gagctgcagg ccttcaagac ggccagggat     180
gcctttgaag actcgttctt gccaaaggac tgggactgca gcacccacct tttccccagg     240
acccgggacc tgaagcacct gcaggtgtgg gagcgccctg tggctctgga ggcagagctg     300
gccctgacac tgacggtcct ggaggccatg gctaactcat ccctgggcca cagcctggag     360 cagcccttc tcacgctgca gaacatccac tccaagctcc aggcctgtgt cccagctcag     420
cccacagcaa gctccaggcc ccggggccgc ctccaccact ggctgcaccg cctccaggag     480
gcccggaagg agtcccagga ctgcctcgaa gcctctgtga tgttcaacct cctccgcctc     540
ctcacccggg acctgaaatg tgttgccagc ggagaccagt gtgtctga                 588

<210> SEQ ID NO 2
<211> LENGTH: 195
<212> TYPE: PRT
```

<213> ORGANISM: Bos taurus

<400> SEQUENCE: 2

| Met | Ala | Pro | Gly | Cys | Thr | Leu | Val | Leu | Val | Leu | Met | Leu | Thr | Thr | Val |
| 1 | | | | 5 | | | | | 10 | | | | | 15 | |

| Ala | Leu | Ser | Arg | Thr | Gly | Ala | Val | Pro | Val | Pro | Ser | Ala | Pro | Arg | Ala |
| | | | 20 | | | | | 25 | | | | | 30 | | |

| Leu | Pro | Pro | Ala | Arg | Gly | Cys | His | Val | Ala | Gln | Phe | Lys | Ser | Leu | Ser |
| | | 35 | | | | | 40 | | | | | 45 | | | |

| Pro | Gln | Glu | Leu | Gln | Ala | Phe | Lys | Thr | Ala | Arg | Asp | Ala | Phe | Glu | Asp |
| | 50 | | | | | 55 | | | | | 60 | | | | |

| Ser | Phe | Leu | Pro | Lys | Asp | Trp | Asp | Cys | Ser | Thr | His | Leu | Phe | Pro | Arg |
| 65 | | | | | 70 | | | | | 75 | | | | | 80 |

| Thr | Arg | Asp | Leu | Lys | His | Leu | Gln | Val | Trp | Glu | Arg | Pro | Val | Ala | Leu |
| | | | | 85 | | | | | 90 | | | | | 95 | |

| Glu | Ala | Glu | Leu | Ala | Leu | Thr | Leu | Thr | Val | Leu | Glu | Ala | Met | Ala | Asn |
| | | | | 100 | | | | | 105 | | | | | 110 | |

| Ser | Ser | Leu | Gly | His | Ser | Leu | Glu | Gln | Pro | Leu | Leu | Thr | Leu | Gln | Asn |
| | | | 115 | | | | | 120 | | | | | 125 | | |

| Ile | His | Ser | Lys | Leu | Gln | Ala | Cys | Val | Pro | Ala | Gln | Pro | Thr | Ala | Ser |
| | 130 | | | | | 135 | | | | | 140 | | | | |

| Ser | Arg | Pro | Arg | Gly | Arg | Leu | His | His | Trp | Leu | His | Arg | Leu | Gln | Glu |
| 145 | | | | 150 | | | | | 155 | | | | | 160 | |

| Ala | Arg | Lys | Glu | Ser | Gln | Asp | Cys | Leu | Glu | Ala | Ser | Val | Met | Phe | Asn |
| | | | | 165 | | | | | 170 | | | | | 175 | |

| Leu | Leu | Arg | Leu | Leu | Thr | Arg | Asp | Leu | Lys | Cys | Val | Ala | Ser | Gly | Asp |
| | | | 180 | | | | | 185 | | | | | 190 | | |

| Gln | Cys | Val |
| | | 195 |

<210> SEQ ID NO 3
<211> LENGTH: 599
<212> TYPE: DNA
<213> ORGANISM: Bos taurus

<400> SEQUENCE: 3

```
gaaccagcga catggccccg ggccgcacgc tggtgctggt gctgatgctg acgaccgtgg      60
cgctgagcag gacaggagca gttcctgtgc cctctgcccc agggccctc  ccacctgcca     120
ggggctgcca catggcccag ttcaagtctc tgtccctca agagctgcag gccttcaaga     180
cggccaggga tgcctttgaa gactcgttct gccaaaggga ctgggactgc agcacccacc     240
ttttccccag gacccgggac ctgaagcacc tgcaggtgtg ggagcgccct gtggctctgg     300
aggcagagct ggccctgaca ctgacggtcc tggaggccat ggctaactca tccctgggcc     360
acagcctgga gcagcccctt ctcacgctgc agaacatcca ctccaagctc caggcctgtg     420
tcccagctca gccacagca agctccaggc ccgggggccg cctccaccac tggctgcacc     480
gcctccagga ggcccggaag gagtcccagg actgcctcga agcctctgtg atgttcaacc     540
tcctccgcct cctcacccgg gacctgaaat gtgttgccag cggagaccag tgtgtctga     599
```

<210> SEQ ID NO 4
<211> LENGTH: 252
<212> TYPE: PRT
<213> ORGANISM: Bos taurus

<400> SEQUENCE: 4

```
Met Pro Pro Pro Leu Arg Leu Asp Pro Glu Arg Ser Glu Arg Arg Ala
1               5                   10                  15

Ala Gly Ala Ala Leu Leu Arg Gly Leu Thr Glu Pro Gly Gly Leu Ser
            20                  25                  30

Ala Ser Thr Arg Met Arg Trp Cys Leu Arg Arg Ser Phe Leu Lys Asp
        35                  40                  45

Gln Glu Glu Ser Pro Gly Thr Ser Asp Met Ala Pro Gly Arg Thr Leu
    50                  55                  60

Val Leu Val Leu Met Leu Thr Thr Val Ala Leu Ser Arg Thr Gly Ala
65                  70                  75                  80

Val Pro Val Pro Ser Ala Pro Arg Ala Leu Pro Pro Ala Arg Gly Cys
                85                  90                  95

His Met Ala Gln Phe Lys Ser Leu Ser Pro Gln Glu Leu Gln Ala Phe
                100                 105                 110

Lys Thr Ala Arg Asp Ala Phe Glu Asp Ser Phe Leu Pro Lys Asp Trp
            115                 120                 125

Asp Cys Ser Thr His Leu Phe Pro Arg Thr Arg Asp Leu Lys His Leu
    130                 135                 140

Gln Val Trp Glu Arg Pro Val Ala Leu Glu Ala Glu Leu Ala Leu Thr
145                 150                 155                 160

Leu Thr Val Leu Glu Ala Met Ala Asn Ser Ser Leu Gly His Ser Leu
                165                 170                 175

Glu Gln Pro Leu Leu Thr Leu Gln Asn Ile His Ser Lys Leu Gln Ala
            180                 185                 190

Cys Val Pro Ala Gln Pro Thr Ala Ser Ser Arg Pro Arg Gly Arg Leu
        195                 200                 205

His His Trp Leu His Arg Leu Gln Glu Ala Arg Lys Glu Ser Gln Asp
    210                 215                 220

Cys Leu Glu Ala Ser Val Met Phe Asn Leu Leu Arg Leu Leu Thr Arg
225                 230                 235                 240

Asp Leu Lys Cys Val Ala Ser Gly Asp Gln Cys Val
                245                 250

<210> SEQ ID NO 5
<211> LENGTH: 591
<212> TYPE: DNA
<213> ORGANISM: Bos taurus

<400> SEQUENCE: 5
atgaccgggg actgcatgcc agtgctggtg ctgatggccg cagtgctgac cgtgactgga      60
gcagttcctg tcgccaggct ccgcggggct ctcccggatg caaggggctg ccacatagcc     120
cagttcaagt ccctgtctcc acaggagctg caggccttta gagggccaa agatgcctta      180 gaagagtcgc ttctgctgaa ggactgcaag tgccgctccc gcctcttccc caggacctgg     240
gacctgaggc agctgcaggt gagggagcgc ccgtggcctt ggaggctga gctggccctg      300 acgctgaagg ttctggaggc caccgctgac actgacccag ccctggggga tgtcttggac     360
cagccccttc acaccctgca ccatatcctc tcccagctcc gggcctgtat ccagcctcag     420
cccacggcag ggcccaggac ccggggccgc ctccaccatt ggctgcaccg gctccaggag     480
gccccaaaaa aggagtcccc tggctgcctc gaggcctctg tcaccttcaa cctcttccgc     540
ctcctcacgc gagacctgaa ttgtgttgcc agcggggacc tgtgtgtctg a              591

<210> SEQ ID NO 6
<211> LENGTH: 193
```

```
<212> TYPE: PRT
<213> ORGANISM: Bos taurus

<400> SEQUENCE: 6

Met Leu Leu Leu Leu Leu Pro Leu Leu Leu Ala Ala Val Leu Thr Arg
1               5                   10                  15

Thr Gln Ala Asp Pro Val Pro Arg Ala Thr Arg Leu Pro Val Glu Ala
            20                  25                  30

Lys Asp Cys His Ile Ala Gln Phe Lys Ser Leu Ser Pro Lys Glu Leu
        35                  40                  45

Gln Ala Phe Lys Lys Ala Lys Gly Ala Ile Glu Lys Arg Leu Leu Glu
    50                  55                  60

Lys Asp Met Arg Cys Ser Ser His Leu Ile Ser Arg Ala Trp Asp Leu
65                  70                  75                  80

Lys Gln Leu Gln Val Gln Glu Arg Pro Lys Ala Leu Gln Ala Glu Val
                85                  90                  95

Ala Leu Thr Leu Lys Val Trp Glu Asn Ile Asn Asp Ser Ala Leu Thr
            100                 105                 110

Thr Ile Leu Gly Gln Pro Leu His Thr Leu Ser His Ile His Ser Gln
        115                 120                 125

Leu Gln Thr Cys Thr Gln Leu Gln Ala Thr Ala Glu Pro Lys Pro Pro
    130                 135                 140

Ser Arg Arg Leu Ser Arg Trp Leu His Arg Leu Gln Glu Ala Gln Ser
145                 150                 155                 160

Lys Glu Thr Pro Gly Cys Leu Glu Asp Ser Val Thr Ser Asn Leu Phe
                165                 170                 175

Gln Leu Leu Leu Arg Asp Leu Lys Cys Val Ala Ser Gly Asp Gln Cys
            180                 185                 190

Val

<210> SEQ ID NO 7
<211> LENGTH: 581
<212> TYPE: DNA
<213> ORGANISM: Bos taurus

<400> SEQUENCE: 7
atgctcctcc tgctgttgcc tctgctgctg gccgcagtgc tgacaagaac ccaagctgac    60
cctgtcccca gggccaccag gctcccagtg aagcaaagg attgccacat tgctcagttc    120
aagtctctgt ccccaaaaga gctgcaggcc ttcaaaaagg ccaagggtgc catcgagaag    180
aggctgcttg agaaggacat gaggtgcagt tcccacctca tctccagggc ctgggacctg    240
aagcagctgc aggtccaaga gcgccccaag gccttgcagg ctgaggtggc cctgaccctg    300
aaggtctggg agaacataaa tgactcagcc ctgaccacca tcctgggcca gcctcttcat    360
acactgagcc acattcactc ccagctgcag acctgtacac agcttcaggc cacagcagag    420
cccaagcccc cgagtcgccg cctctcccgc tggctgcaca ggctccagga ggcccagagc    480
aaggagactc ctggctgcct ggaggactct gtcacctcca acctgtttca actgctcctc    540
cgggacctca gtgtgtggcc agtggagacc agtgtgtctg a                       581

<210> SEQ ID NO 8
<211> LENGTH: 195
<212> TYPE: PRT
<213> ORGANISM: Bos taurus

<400> SEQUENCE: 8
```

Met Ala Leu Gly Gly Ser Leu Val Leu Val Leu Met Thr Val
1               5                   10                  15

Ala Pro Pro Arg Thr Gly Ala Val Pro Val Pro Glu Ala Leu Arg Ala
            20                  25                  30

Leu Pro Gly Ala Arg Gly Cys His Leu Ala Gln Phe Lys Ser Leu Ser
        35                  40                  45

Pro Gln Ala Leu Gln Ala Phe Lys Arg Ala Lys Asp Ala Phe Glu Glu
    50                  55                  60

Ser Leu Leu Glu Asp Trp Asn Cys Ser Ser Arg Ile Phe Pro Arg Ser
65                  70                  75                  80

Arg Asp Leu Lys Gln Leu Gln Val Trp Glu Arg Pro Val Ala Leu Glu
                85                  90                  95

Ala Glu Val Ala Leu Thr Leu Ser Val Leu Gly Ser Leu Ala Asn Ser
            100                 105                 110

Ser Leu His Ser Ser Leu Asp Gln Pro Leu His Thr Leu Arg His Ile
        115                 120                 125

His Ala Gln Leu Gln Ala Cys Val Pro Ala Gln Pro Met Ala Gly Pro
    130                 135                 140

Arg Pro Arg Gly Arg Leu His His Trp Leu His Arg Leu Gln Glu Ala
145                 150                 155                 160

Gln Lys Lys Glu Pro Gln Ser Cys Leu Glu Ala Ser Val Met Phe Asn
                165                 170                 175

Leu Phe Arg Leu Leu Thr Arg Asp Leu Lys Cys Val Ala Ser Gly Asp
            180                 185                 190

Leu Cys Val
        195

<210> SEQ ID NO 9
<211> LENGTH: 588
<212> TYPE: DNA
<213> ORGANISM: Bos taurus

<400> SEQUENCE: 9
atggccctgg gtggctcgct ggtgctggtg ctggtgctga tgacggtggc tccacccagg      60
acaggagcgg tgcctgtccc tgaagccctc agggccctcc caggagcaag gggctgccac     120
ttggcccagt tcaagtctct gtccccacaa gcgctgcagg ccttcaagag gccaaggat      180 gcctttgaag agtccctctt ggaggactgg aactgcagct cccgcatctt ccccaggagc     240
agggacctga gcagctgca ggtgtgggag cgcccccgtgg ccttggaggc cgaggtggcc     300
ctgaccctca gcgtcctggg ctccttggcg aactcatccc tgcacagcag cctggaccag     360
ccccttcaca cgctgcgcca catccacgcc cagctccagg cctgtgtccc agctcagccc     420
atggcaggcc cccggccccg gggccgcctc caccactggc tgcaccggct ccaggaggcc     480
cagaagaagg agccccagag ctgcctggaa gcctctgtca tgttcaacct cttccgcctc     540
ctcacccggg acctgaaatg tgtcgccagt ggagacctgt gtgtctga                 588

<210> SEQ ID NO 10
<211> LENGTH: 200
<212> TYPE: PRT
<213> ORGANISM: Bos taurus

<400> SEQUENCE: 10

Met Lys Leu Asp Met Thr Gly Asp Cys Met Pro Val Leu Val Leu Met
1               5                   10                  15

Ala Ala Val Leu Thr Val Thr Gly Ala Val Pro Val Ala Arg Leu Arg

```
                20                  25                  30
Gly Ala Leu Pro Asp Ala Arg Gly Cys His Ile Ala Gln Phe Lys Ser
            35                  40                  45

Leu Ser Pro Gln Glu Leu Gln Ala Phe Lys Arg Ala Lys Asp Ala Leu
        50                  55                  60

Glu Glu Ser Leu Leu Leu Lys Asp Cys Lys Cys Arg Ser Arg Leu Phe
65                  70                  75                  80

Pro Arg Thr Trp Asp Leu Arg Gln Leu Gln Val Arg Glu Arg Pro Val
                85                  90                  95

Ala Leu Glu Ala Glu Leu Ala Leu Thr Leu Lys Val Leu Glu Ala Thr
            100                 105                 110

Ala Asp Thr Asp Pro Ala Leu Gly Asp Val Leu Asp Gln Pro Leu His
        115                 120                 125

Thr Leu His His Ile Leu Ser Gln Leu Arg Ala Cys Ile Gln Pro Gln
    130                 135                 140

Pro Thr Ala Gly Pro Arg Thr Arg Gly Arg Leu His His Trp Leu His
145                 150                 155                 160

Arg Leu Gln Glu Ala Pro Lys Lys Glu Ser Pro Gly Cys Leu Glu Ala
                165                 170                 175

Ser Val Thr Phe Asn Leu Phe Arg Leu Leu Thr Arg Asp Leu Asn Cys
            180                 185                 190

Val Ala Ser Gly Asp Leu Cys Val
        195                 200

<210> SEQ ID NO 11
<211> LENGTH: 818
<212> TYPE: DNA
<213> ORGANISM: Bos taurus

<400> SEQUENCE: 11
attgggccct ctagatgcat gctcgagcgg ccgccagtgt gatggatatc tgcagaattc     60
gcccttcccc tcaccttcct atgcttcctt aaccagacat ggccccgggc tgcacgctgg    120
tgctggtgct gatgctgacg accgtggcgc tgagcaggac aggagcagtt cctgtgccct    180
ctgcccccag ggccctccca cctgccaggg gctgccacgt ggcccagttc aagtctctgt    240
cccctcaaga gctgcaggcc ttcaagacgg ccagggatgc ctttgaagac tcgttcttgc    300
caaaggactg ggactgcagc acccaccttt tccccaggac ccgggacctg aagcacctgc    360
aggtgtggga gcgccctgtg gctctggagg cagagctggc cctgacactg acggtcctgg    420
aggccatggc taactcatcc ctgggccaca gcctggagca gccccttctc acgctgcaga    480
acatccactc caagctccag gcctgtgtcc cagctcagcc cacagcaagc tccaggcccc    540
ggggccgcct ccaccactgg ctgcaccgcc tccaggaggc ccgaaggag tcccaggact    600 gcctcgaagc ctctgtgatg ttcaacctcc tccgcctcct cacccgggac ctgaaatgtg    660
ttgccagcgg agaccagtgt gtctgacccc agagacctgc ctgcaacctg tcctaccttt    720
ttagatattt ttttatgcat caaaatcagt tttttttta tttattgcct ccaaataatt    780
atttatttat agatgacatt tctcaaactc agacccag                           818

<210> SEQ ID NO 12
<211> LENGTH: 26
<212> TYPE: DNA
<213> ORGANISM: Artificial Sequence
<220> FEATURE:
<223> OTHER INFORMATION: Chemically Synthesized
```

<400> SEQUENCE: 12
atcgatatgg ccccgggctg cacgct                                            26

<210> SEQ ID NO 13
<211> LENGTH: 30
<212> TYPE: DNA
<213> ORGANISM: Artificial Sequence
<220> FEATURE:
<223> OTHER INFORMATION: Chemically Synthesized

<400> SEQUENCE: 13
tctagattag acacactggt ctccgctggc                                        30

<210> SEQ ID NO 14
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 14
gctactcaca gtagctgcct tcag                                              24

<210> SEQ ID NO 15
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 15
agccaggtct tctcggcac                                                    19

<210> SEQ ID NO 16
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 16
ccagtattct tgtgggcttc aca                                               23

<210> SEQ ID NO 17
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 17
gtcattcctg caagtcaatc ctg                                               23

<210> SEQ ID NO 18
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 18
gcatcgtgga gggacttatg a                                                 21

<210> SEQ ID NO 19
<211> LENGTH: 22

<212> TYPE: DNA
<213> ORGANISM: Artificial Sequence
<220> FEATURE:
<223> OTHER INFORMATION: Chemically Synthesized

<400> SEQUENCE: 19
ctacagcttg cttcgattcc aa                                    22

<210> SEQ ID NO 20
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 20
tttgacaaac tgagcgtcat ca                                    22

<210> SEQ ID NO 21
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 21
ccagctgccg cattgtct                                         18

<210> SEQ ID NO 22
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 22
actcatccct gggccaca                                         18

<210> SEQ ID NO 23
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 23
ggactgtgac acgcccatct                                       20

<210> SEQ ID NO 24
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 24
gcgtgtacaa gcggaccagt                                       20

<210> SEQ ID NO 25
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 25
aggagtcaaa gcccaccatc t                                           21

<210> SEQ ID NO 26
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 26
cgtccggagc acgaagaa                                               18

<210> SEQ ID NO 27
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 27
ccaaagttgt gaagggtggc                                             20

<210> SEQ ID NO 28
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 28
tgccaaactg gcttatgaaa ag                                          22

<210> SEQ ID NO 29
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 29
acacgtcaca tttgcggaaa                                             20

<210> SEQ ID NO 30
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 30
gcgacttggg agttaattgc a                                           21

<210> SEQ ID NO 31
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 31
agaagcagca ggccgttg                                               18

<210> SEQ ID NO 32
<211> LENGTH: 25
<212> TYPE: DNA
<213> ORGANISM: Artificial Sequence

```
<220> FEATURE:
<223> OTHER INFORMATION: Chemically Synthesized

<400> SEQUENCE: 32
ggtgtaaaag acaactgcat tgatg                                              25

<210> SEQ ID NO 33
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 33
cccattcttt ttcattgtgg c                                                  21

<210> SEQ ID NO 34
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 34
gggccatcca cagtcttctg                                                    20

<210> SEQ ID NO 35
<211> LENGTH: 20
<212> TYPE: DNA
<213> ORGANISM: Artificial Sequence
<220> FEATURE:
<223> OTHER INFORMATION: Chemically Synthesized

<400> SEQUENCE: 35
ctgccccagg agtttctgac                                                    20

<210> SEQ ID NO 36
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 36
cggccccagg gttca                                                         15

<210> SEQ ID NO 37
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 37
tccttccaga aattcacctc atagt                                              25

<210> SEQ ID NO 38
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 38
gcttggagtg gatgttctgc a                                                  21
```

```
<210> SEQ ID NO 39
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 39
cccggaactc cagcagttc                                                   19

<210> SEQ ID NO 40
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 40
agcgggtgct catcatcc                                                    18

<210> SEQ ID NO 41
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 41
ttctgtgtca tgggcttgaa ct                                               22

<210> SEQ ID NO 42
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 42
cgtccggagc acgaagaa                                                    18

<210> SEQ ID NO 43
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 43
tgatcgtccc ctgagggtc                                                   19

<210> SEQ ID NO 44
<211> LENGTH: 19
<212> TYPE: DNA
<213> ORGANISM: Artificial Sequence
<220> FEATURE:
<223> OTHER INFORMATION: Chemically Synthesized

<400> SEQUENCE: 44
tcaccacacg cagcactga                                                   19

<210> SEQ ID NO 45
<211> LENGTH: 20
<212> TYPE: DNA
<213> ORGANISM: Artificial Sequence
<220> FEATURE:
<223> OTHER INFORMATION: Chemically Synthesized
```

```
<400> SEQUENCE: 45
catccgtgca tcctcattga                                              20

<210> SEQ ID NO 46
<211> LENGTH: 21
<212> TYPE: DNA
<213> ORGANISM: Artificial Sequence
<220> FEATURE:
<223> OTHER INFORMATION: Chemically Synthesized

<400> SEQUENCE: 46
ccgaggtgct cgctcagcca g                                            21

<210> SEQ ID NO 47
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 47
atttggcgct gacacc                                                  16

<210> SEQ ID NO 48
<211> LENGTH: 24
<212> TYPE: DNA
<213> ORGANISM: Artificial Sequence
<220> FEATURE:
<223> OTHER INFORMATION: Chemically Synthesized

<400> SEQUENCE: 48
agcagctggc caatgaagcc tgtg                                         24

<210> SEQ ID NO 49
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 49
ccacgtgtcg agatta                                                  16

<210> SEQ ID NO 50
<211> LENGTH: 23
<212> TYPE: DNA
<213> ORGANISM: Artificial Sequence
<220> FEATURE:
<223> OTHER INFORMATION: Chemically Synthesized

<400> SEQUENCE: 50
cactgtccac gccatcactg cca                                          23

<210> SEQ ID NO 51
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 51
acgtcagagc cttaaa                                                  16

<210> SEQ ID NO 52
```

<211> LENGTH: 19
<212> TYPE: DNA
<213> ORGANISM: Artificial Sequence
<220> FEATURE:
<223> OTHER INFORMATION: Chemically Synthesized

<400> SEQUENCE: 52
aagtgtctga aagctgcaa                                              19

<210> SEQ ID NO 53
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 53
ccccaaccag atatg                                                  15

<210> SEQ ID NO 54
<211> LENGTH: 22
<212> TYPE: DNA
<213> ORGANISM: Artificial Sequence
<220> FEATURE:
<223> OTHER INFORMATION: Chemically Synthesized

<400> SEQUENCE: 54
cctggagcag ccccttctca cg                                          22

<210> SEQ ID NO 55
<211> LENGTH: 15
<212> TYPE: DNA
<213> ORGANISM: Artificial Sequence
<220> FEATURE:
<223> OTHER INFORMATION: Chemically Synthesized

<400> SEQUENCE: 55
acttcggcac cttct                                                  15

<210> SEQ ID NO 56
<211> LENGTH: 25
<212> TYPE: DNA
<213> ORGANISM: Artificial Sequence
<220> FEATURE:
<223> OTHER INFORMATION: Chemically Synthesized

<400> SEQUENCE: 56
ctggctgtct tttgaaggga ggccc                                       25

<210> SEQ ID NO 57
<211> LENGTH: 16
<212> TYPE: DNA
<213> ORGANISM: Artificial Sequence
<220> FEATURE:
<223> OTHER INFORMATION: Chemically Synthesized

<400> SEQUENCE: 57
attggcgctg gacaca                                                 16

<210> SEQ ID NO 58
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 58

```
cgtccggagc acgaagaa                                                  18

<210> SEQ ID NO 59
<211> LENGTH: 13
<212> TYPE: DNA
<213> ORGANISM: Artificial Sequence
<220> FEATURE:
<223> OTHER INFORMATION: Chemically Synthesized

<400> SEQUENCE: 59
ctcaggcaaa ggc                                                       13

<210> SEQ ID NO 60
<211> LENGTH: 18
<212> TYPE: DNA
<213> ORGANISM: Artificial Sequence
<220> FEATURE:
<223> OTHER INFORMATION: Chemically Synthesized

<400> SEQUENCE: 60
cagaacaatg agagatgg                                                  18

<210> SEQ ID NO 61
<211> LENGTH: 17
<212> TYPE: DNA
<213> ORGANISM: Artificial Sequence
<220> FEATURE:
<223> OTHER INFORMATION: Chemically Synthesized

<400> SEQUENCE: 61
acaatgatgc cctcatt                                                   17
```